(12) United States Patent
Chaudry

(10) Patent No.: US 9,808,471 B2
(45) Date of Patent: *Nov. 7, 2017

(54) NASAL PHARMACEUTICAL FORMULATIONS AND METHODS OF USING THE SAME

(75) Inventor: Imtiaz Chaudry, Napa, CA (US)

(73) Assignee: Mylan Specialty LP, Canonsburg, PA (US)

( * ) Notice: Subject to any disclaimer, the term of this patent is extended or adjusted under 35 U.S.C. 154(b) by 659 days.

This patent is subject to a terminal disclaimer.

(21) Appl. No.: 10/414,682

(22) Filed: Apr. 16, 2003

(65) Prior Publication Data

US 2004/0208830 A1    Oct. 21, 2004

(51) Int. Cl.

| A61K 9/14 | (2006.01) |
|---|---|
| A61K 9/12 | (2006.01) |
| A61K 31/56 | (2006.01) |
| A61K 31/573 | (2006.01) |
| A61K 9/00 | (2006.01) |
| A61K 31/57 | (2006.01) |
| A61K 31/7048 | (2006.01) |
| A61L 2/00 | (2006.01) |
| A61K 9/10 | (2006.01) |

(52) U.S. Cl.
CPC .......... *A61K 31/573* (2013.01); *A61K 9/0043* (2013.01); *A61K 31/56* (2013.01); *A61K 31/57* (2013.01); *A61K 31/7048* (2013.01); *A61L 2/0035* (2013.01); *A61K 9/10* (2013.01)

(58) Field of Classification Search
CPC .... A61K 31/56; A61K 31/132; A61K 31/185; A61K 2039/543; A61K 9/10; A61K 31/573
USPC ................................. 514/169, 958
See application file for complete search history.

(56) References Cited

U.S. PATENT DOCUMENTS

| 2,989,437 A | 6/1961 | Wruble et al. |
|---|---|---|
| 3,091,569 A | 5/1963 | Sheffner |
| 5,174,475 A | 12/1992 | Day et al. |
| 5,593,688 A | 1/1997 | Baldeschwieler |
| 5,858,330 A | 1/1999 | Boltri et al. |
| 5,958,378 A | 9/1999 | Waldrep et al. |
| 5,976,573 A | 11/1999 | Kim |
| 5,993,781 A | 11/1999 | Snell et al. |
| 6,113,894 A | 9/2000 | Smith |
| 6,207,703 B1 | 3/2001 | Ponikau |
| 6,241,969 B1 | 6/2001 | Saidi et al. |
| 6,291,500 B2 | 9/2001 | Ponikau |
| 6,368,616 B1 | 4/2002 | Doi |
| 6,410,062 B1 | 6/2002 | Callaghan et al. |
| 6,464,958 B1 | 10/2002 | Bernini et al. |
| 6,465,709 B1 | 10/2002 | Sun et al. |
| 6,509,028 B2 | 1/2003 | Williams et al. |
| 6,555,566 B2 | 4/2003 | Ponikau |
| 6,608,054 B2 * | 8/2003 | Meade et al. ............ 514/229.5 |
| 6,686,346 B2 | 2/2004 | Nilsson et al. |
| 7,811,606 B2 | 10/2010 | Chaudry |
| 7,972,626 B2 | 7/2011 | Chaudry |
| 7,972,627 B2 | 7/2011 | Chaudry |
| 8,129,364 B2 | 3/2012 | Chaudry |
| 8,158,154 B2 | 4/2012 | Chaudry |
| 8,309,061 B2 | 11/2012 | Chaudry |
| 8,663,695 B2 | 3/2014 | Chaudry |
| 8,912,174 B2 | 12/2014 | Chaudry |
| 2001/0002404 A1 | 5/2001 | Webb et al. |
| 2001/0008632 A1 | 7/2001 | Freund et al. |
| 2002/0006944 A1 | 1/2002 | Ohkawa et al. |
| 2002/0010208 A1 | 1/2002 | Shashoua et al. |
| 2002/0013331 A1 | 1/2002 | Williams et al. |
| 2002/0052390 A1 | 5/2002 | Ponikau |
| 2002/0061281 A1 | 5/2002 | Osbakken et al. |
| 2002/0071874 A1 | 6/2002 | Olejnik et al. |
| 2002/0124820 A1 | 9/2002 | Kreuter et al. |
| 2002/0136918 A1 | 9/2002 | Akutsu et al. |
| 2002/0177609 A1 | 11/2002 | Swindell et al. |
| 2002/0192288 A1 | 12/2002 | Williams et al. |
| 2002/0198209 A1 | 12/2002 | Woodward et al. |
| 2003/0007930 A1* | 1/2003 | Bot et al. .................. 424/45 |
| 2003/0017199 A1 | 1/2003 | Woodward et al. |
| 2003/0065023 A1 | 4/2003 | Swindell et al. |
| 2003/0222364 A1 | 12/2003 | Jackson et al. |
| 2004/0045805 A1 | 3/2004 | Lancaster et al. |
| 2004/0081626 A1 | 4/2004 | Watanabe et al. |
| 2004/0136918 A1 | 7/2004 | Garrett et al. |
| 2004/0141925 A1 | 7/2004 | Bosch et al. |
| 2004/0208831 A1 | 10/2004 | Chaudry |
| 2004/0208833 A1 | 10/2004 | Hovey et al. |
| 2007/0140980 A1 | 6/2007 | Capocchi et al. |
| 2008/0050442 A1 | 2/2008 | Chaudry |

FOREIGN PATENT DOCUMENTS

| CA | 2 522 291 A1 | 10/2004 |
|---|---|---|
| CA | 2 522 292 A1 | 10/2004 |

(Continued)

OTHER PUBLICATIONS

Drug Information Handbook, C. Lacy et al., Lexi-Comp, Inc., Cleveland, 1993, pp. 397.

(Continued)

*Primary Examiner* — Shobha Kantamneni

(57) ABSTRACT

Nasal pharmaceutical formulations comprising a drug substance having a specific particle size distribution profile are disclosed herein. Such profile provides increased bioavailability, increased efficacy or prolonged therapeutic effect of the drug substance when administered intranasally. The formulations of the present invention may comprise one or more corticosteroids having a specific particle size distribution profile. In a preferred embodiment, the corticosteroid is fluticasone or a pharmaceutically acceptable derivative thereof for the treatment of one or more symptoms of rhinitis. Preferably, the drug substance is fluticasone propionate. The formulations herein may be provided as an aqueous suspension suitable for inhalation via the intranasal route.

17 Claims, 4 Drawing Sheets

(56) References Cited

FOREIGN PATENT DOCUMENTS

| | | |
|---|---|---|
| CN | 1282251 A | 1/2001 |
| CN | 1335766 A | 2/2002 |
| CN | 1409627 A | 4/2003 |
| EP | 0 343 268 | 11/1989 |
| EP | 0 385 445 A2 | 9/1990 |
| GB | 2 107 715 | 5/1983 |
| JP | 1-100120 A | 4/1989 |
| JP | 03-165833 | 7/1991 |
| JP | 5-506642 | 9/1993 |
| JP | 06-506231 A | 7/1994 |
| JP | 07-053358 | 2/1995 |
| JP | 10-500420 | 1/1998 |
| JP | 11-130659 A | 5/1999 |
| JP | 11-514979 A | 12/1999 |
| JP | 2000-508675 A | 7/2000 |
| JP | 2001-002589 | 1/2001 |
| JP | 2001-520188 A | 10/2001 |
| JP | 2001-523638 | 11/2001 |
| JP | 2002-528484 A | 9/2002 |
| JP | 2002-529396 A | 9/2002 |
| JP | 2002-539154 | 11/2002 |
| JP | 2003-506396 | 2/2003 |
| JP | 2003-512892 A | 4/2003 |
| JP | 2003-519171 A | 6/2003 |
| JP | 2004-500435 A | 1/2004 |
| JP | 2004-500984 A | 1/2004 |
| JP | 2004-520432 A | 7/2004 |
| JP | 2005-503378 | 2/2005 |
| JP | 2005-506369 | 3/2005 |
| JP | 4718445 | 7/2011 |
| KR | 2003-0045246 | 6/2003 |
| KR | 2006-0003009 | 1/2006 |
| KR | 2006-0003010 | 1/2006 |
| WO | WO 86/03750 | 7/1986 |
| WO | WO 92/04365 | 8/1992 |
| WO | WO 92/17183 | 10/1992 |
| WO | WO 95/31964 A1 | 11/1995 |
| WO | WO 97/08950 A1 | 3/1997 |
| WO | WO 99/18971 | 4/1999 |
| WO | WO 99/20261 A2 | 4/1999 |
| WO | WO 00/12063 A1 | 3/2000 |
| WO | WO 00/25746 | 5/2000 |
| WO | WO 00/27363 | 5/2000 |
| WO | WO 01/10409 A1 | 2/2001 |
| WO | WO 01/13885 A1 | 3/2001 |
| WO | WO 01/32125 | 5/2001 |
| WO | WO 01/49263 | 7/2001 |
| WO | WO 01/78743 A1 | 10/2001 |
| WO | WO 02/00199 | 1/2002 |
| WO | WO-02/053186 A2 | 7/2002 |
| WO | WO 02/055136 A2 | 7/2002 |
| WO | WO 02/072066 A1 | 9/2002 |
| WO | WO 03/013434 A2 | 2/2003 |
| WO | WO 03/020219 A2 | 3/2003 |
| WO | WO 03/035062 A1 | 5/2003 |

OTHER PUBLICATIONS

Family Practice Notebook.com—Systematic Corticosteroid—http://www.fpnotebook.com/END188.htm.
Family Practice Notebook.com—Allergic Fungal Sinusitis—http://www.fpnotebook.com/ENT151.htm.
Family Practice Notebook.com—Inhaled Corticosteroid—http://www.fpnotebook.com/LUN112.htm.
Americas Family Physician—Jan. 1, 2001—Adult Rhinosinusitis: Diagnosis and Management—J. David Osguthorpe, M.D., Medical University of South Carolina, Charleston, South Carolina—http://www.aafp.org/afp/20010101/69.html.
The Diagnosis and Incidence of Allergic Fungal Sinusitis—Jens U. Ponikau, MD; David A. Sherris, MD; Eugene B. Kern, MD; Henry A. Homburger, MD; Evangelos Frigas, MD; Thomas A. Gaffey, MD; and Glenn D. Robers, PhD—1999 Mayo Foundation for Medical Education and Research—May Clin. Proc, Sep. 1999, vol. 74.
UTMB—The University of Texas Medical Branch—Rhinosinusitis: Current Concepts; Frederick S. Rosen, MD, Mathew Ryan MD.
Allergic Diseases Resource Center: Rhinosinusitis—Rhinosinusitis: Synopsis http://www.worldallergy.org/professional/allergic_deseases_center/rhinosinusitis/sinusitiss . . . .
Mayo Clinic, Rochester, Minnesota—Mayo Clinic Receives Patent for New Treatment of Chronic Sinus Infection Apr. 30, 2003—http://www.mayclinic.org/news2003-rst/1772.html.
NCBI—PubMed—Improved method for estimation of azole antifungal inhibitory concentrations against *Candida* Species, based on azole/antibiotic interactions; Odds FC, Abbot AB, Pye G., Troke PF.; Mar. 17, 2003.
NCBI—PubMed—Chronic invasive fungal rhinosinusitis—Stringer SP, Ryan MW; http://www.ncbi.nlm.nih.gov/entrez/query.fcgi?cmd_Retrieve&db=PubMed&List_uids-10 . . . .
NCBI—PubMed—Acute invasive fungal rhinosinusitis—case report; Jedrusik A, Galewicz A, Krzeski A, Dwilewicz-Trojaczek J. Deptala A, Michalilc J; http://www.ncbi.nlm.nih.gov/entrez/query.fcgi?cmd_Retrieve&db=PubMed&List_uids-12.
NCBI—PubMed—Intransal antifungal treatment in 51 patients with chronic rhinosinusitis; Ponikau JU, Sherris DA, Kita H, Kern EB; http://www.ncbi.nlm.nih.gov/entrez/query.fcgi?cmd_Retrieve&db=PubMed&List_uids-12.
NCBI—PubMed—Energing and less common fungal pathogens; Fleming RV, Walsh TJ, Anaissie EJ; http://www.ncbi.nlm.nih.gov/entrez/query.fcgi?cmd_Retrieve&db=PubMed&List_uids-12.
NCBI—PubMed—Topical antibiotic antifungal, and antiseptic solutions decrease ciliary activity in nasal respiratory cells; Gosepath J, Grebneva N, Mossikhin S, Mann WJI; http://www.ncbi.nlm.nih.gov/entrez/query.fcgi?cmd_Retrieve&db=PubMed&List_uids-11.
NCBI—PubMed—Chronic invasive final sinusitis: a report of two atypical cases; Busaba NY, Colden DG, Faquin WC, Salman SD; http://www.ncbi.nlm.nih.gov/entrez/query.fcgi?cmd_Retrieve&db=PubMed&List_uids-12.
NCBI—PubMed—Rhinocerebral mucormycosis in the era of lipid-based amphotericin B: case report and literature review; Mondy KE, Haughey B, Custer PL, Wippold FJ 2nd, Ritchie DJ, Mundy LM; http://www.ncbi.nlm.nih.gov/entrez/query.fcgi?cmd_Retrieve&db=PubMed&List_uids-11.
NCBI—PubMed—Effect of anti-fungal nasal lavage with amphotericin B on nasal polyposis; Ricchetti A, Landis BN, Maffioli A, Giger R, Zeng C, Lacroix JS; http://www.ncbi.nlm.nih.gov/entrez/query.fcgi?cmd_Retrieve&db=PubMed&List_uids-11.
NCBI—PubMed—Paranasal sinus mucormycosis: a report of two cases; Ruoppi P, Dietz A, Nikanne E, Seppa J, Markkanen H, Nuutinen J; http://www.ncbi.nlm.nih.gov/entrez/query.fcgi?cmd_Retrieve&db=PubMed&List_uids-11.
NCBI—PubMed—A case report of allergic fungal sinusitis caused by *Penicillium* sp. and *Cladosporium* sp; Matsuwaki Y, Nakajima T, Lida M, Nohara O, Haruna S, Moriyama H http://www.ncbi.nlm.nih.gov/entrez/query.fcgi?cmd_Retrieve&db=PubMed&List_uids-11.
NCBI—PubMed—Acute fulminant fungal sinusitis: clinical presentation, radiological findings and treatment; Sohail MA, Al Khabori M, Hyder J, Verma A; http://www.ncbi.nlm.nih.gov/entrez/query.fcgi?cmd_Retrieve&db=PubMed&List_uids-11.
NCBI—PubMed—Treatment of invasive fungal sinusitis with liposomal amphotericin B: a report of four cases; Sungkanuparph S, Sathpatayavongs B, Kunachak S, Luxameechanporn T, Cheewaruangroj W; http://www.ncbi.nlm.nih.gov/entrez/query.fcgi?cmd_Retrieve&db=PubMed&List_uids-11.
NCBI—PubMed—Fungal infections of the paranasal sinuses; Karci B, Burhanoglu D, Erdem T, Hilmioglu S, Inci R, Veral A; http://www.ncbi.nlm.nih.gov/entrez/query.fcgi?cmd_Retrieve&db=PubMed&List_uids-11.
NCBI—PubMed—Case report. Successful outcome of invasive nasal sinus zygomycosis in a child with relapsed acute lymphoblastic leukaemia due to liposomal ampohtericin B; Wali YA, al LamkiZ, al Kindi H, Taqi AM, Shah W, Soliman H, Zacharia

(56) References Cited

OTHER PUBLICATIONS

M, al Okbi H; http://www.ncbi.nlm.nih.gov/entrez/query.fcgi?cmd_Retrieve&db=PubMed&List_uids-11.
NCBI—PubMed—Aggressive combination treatment for invasive fungal sinusitis in immunocompromised patients; Rizk SS, Krasu DH, gerresheim G, Mudan S; http://www.ncbi.nlm.nih.gov/entrez/query.fcgi?cmd_Retrieve&db=PubMed&List_uids-10.
NCBI—PubMed—Efficacy of FK463, a new lipopeptide antifungal agnet, in mouse models of pulmonary aspergillosis; Matsumoto S, Wakai Y, Nakai T, Hatano K, Ushitani T, Ikeda F, Tawara S, Goto T, Matsumoto F, Kuwahara S; http://www.ncbi.nlm.nih.gov/entrez/query.fcgi?cmd_Retrieve&db=PubMed&List_uids-10.
NCBI—PubMed—Report of two rare cases of fungal sinusitis; Moriyama, Watanabe T, Kodama S, Suzuki M, Mogi G; http://www.ncbi.nlm.nih.gov/entrez/query.fcgi?cmd_Retrieve&db=PubMed&List_uids-10.
NCBI—PubMed—Successful treatment of a invasive aspergillosis of the skull base and paranasal sinuses with liposomal amphotericin B and itraconazole; Streppel M, Bachmann Arnold G, Damm M, Stennert E; http://www.ncbi.nlm.nih.gov/entrez/query.fcgi?cmd_Retrieve&db=PubMed&List_uids-10.
NCBI—PubMed—Successful Treatment of Mucormycosis and *Aspergillus* sp. Rhinosinusitis in an Immunocompromised Patient; Borges V Neto, Medeiros S. Ziomkowki S, Machado A; http://www.ncbi.nlm.nih.gov/entrez/query.fcgi?cmd_Retrieve&db=PubMed&List_uids-11.
NCBI—PubMed—Report of the first case of invasive fungal sinusitis caused by Scopulariopsis acremonium; review of scopulariopsis infections; Ellison MD, Hung RT, Harris K, Campbell BH; http://www.ncbi.nlm.nih.gov/entrez/query.fcgi?cmd_Retrieve&db=PubMed&List_uids-97.
NCBI—PubMed—Successful program to prevent aspergillus infections in children undergoing marrow transplantation: use of nasal amphotericin; Trigg ME, Morgan D, Burns TL, Kook H, Rumelhart SL, Holida MD, Giller RH; http://www.ncbi.nlm.nih.gov/entrez/query.fcgi?cmd_Retrieve&db=PubMed&List_uids-90.
NCBI—PubMed—Aspergillus sinusitis: clinical aspects and treatment outcomes; Min YG, HKim HS, Lee KS, Kang MK, Han MH; http://www.ncbi.nlm.nih.gov/entrez/query.fcgi?cmd_Retrieve&db=PubMed&List_uids-87.
NCBI—PubMed—Antifungal activity against allergic fungal sinusitis organisms; Bent JP 3rd, Kuhn FA; http://www.ncbi.nlm.nih.gov/entrez/query.fcgi?cmd_Retrieve&db=PubMed&List_uids-89.
NCBI—PubMed—Liposomal amphotericin B (AmBisome) in the treatment of complicated kala-azar under filed conditions; Seamans J, Boer C, Wilkinson R, de Jong J, de Wilde E, Sondorp E, Davidson R.
NCBI—Successful treatment of sinusitis caused by Cunninghamella bertholletiae; Ng TT, Campbell CK, Rothera M, Houghton JB, Hughes D, Denning DW; http://www.ncbi.nlm.nih.gov/entrez/query.fcgi?cmd_Retrieve&db=PubMed&List_uids-79.
NCBI—Invasive ottits extema due to *Aspergillus* species: case report and review; Godon G, Gidding NA.
NCBI—PubMed—Invasive fungal sinusitis in patients undergoing bone marrow transplantation; Drakos PE, Nagler A, On R, Naparstek E, Kapelushnik J, Engelhard D, Rahv G, Ne'emean D, Slavin S; http://www.ncbi.nlm.nih.gov/entrez/query.fcgi?cmd_Retrieve&db=PubMed&List_uids-82.
NCBI—PubMed—New methods of delivery of amphotericin B; Schmitt HJ; http://www.ncbi.nlm.nih.gov/entrez/query.fcgi?cmd_Retrieve&db=PubMed&List_uids-82.
NCBI—PubMed—Oral itraconazole plus nasal ampohtericin B for prophylaxis of invasive aspergillosis in patients with hematological malignancies; Todeschini G, Murari C, Boneis R, Pizzolo G, Amaddi G, Ambrosetti A, Ceru S, Piacentini I, Martini N, Montresor P, et al.
NCBI—PubMed—Infection due to the fungus Acremonium (Cephalosporium) Fincher RM, Fisher JF, Lovel RD, Newman CL, Espinel-Ingroff A, Shadomy HJ http://www.ncbi.nlm.nih.gov/entrez/query.fcgi?cmd_Retrieve&db=PubMed&List_uids-19.
NCBI—PubMed—Intranasal ampohtericin B reduces the frequency of invasive aspergillosis in neutropenic patients; Jeffery GM, Beard ME, Ikram RB, Chua J, Allen JB, Heaton DC, Hart DN, Schousboe MI; http://www.ncbi.nlm.nih.gov/entrez/query.fcgi?cmd_Retrieve&db=PubMed&List_uids-20.
NCBI—PubMed—Antifungal and surgical treatment of invasive aspergillosis; review of 2,121 published cases; Denning DW, Stevens DA; http://www.ncbi.nlm.nih.gov/entrez/query.fcgi?cmd_Retrieve&db=PubMed&List_uids-22.
NCBI—PubMed—Intraconazole therapy in aspergillosis: study in 49 patients; Dupont B; http://www.ncbi.nlm.nih.gov/entrez/query.fcgi?cmd_Retrieve&db=PubMed&List_uids-21.
NCBI—PubMed—Comparison of oral fluconazole and amphotericin B prophylaxis against fungal infections in the neutropenic phase of patients treated with antileukemic agents; Finke R; http://www.ncbi.nlm.nih.gov/entrez/query.fcgi?cmd_Retrieve&db=PubMed&List_uids-21.
NCBI—PubMed—Fungal diseases of the sinuses; Corey JP, Romberger CF, Shaw GY; http://www.ncbi.nlm.nih.gov/entrez/query/fcgi?cmd_Retrieve&db=PubMed&List_uids-21.
NCBI—PubMed—Decrease in systematic fungal infections in hematogical neoplasms with empirical use of amphotericin B therapy; Zimmermann-Holsi MB, Stahel RA, Vogt P, Oelz O; http://www.ncbi.nlm.nih.gov/entrez/query.fcgi?cmd_Retrieve&db=PubMed&List_uids-29.
NCBI—PubMed—Allergic fungal sinusitis; Philip G, Keen CE; http://www.ncbi.nlm.nih.gov/entrez/query.fcgi?cmd_Retrieve&db=PubMed&List_uids-27.
NCBI—PubMed—Nonsurgical treatment of sinusitis; Malow IB, Creticos CM; http://www.ncbi.nlm.nih.gov/entrez/query.fcgi?cmd_Retrieve&db=PubMed&List_uids-27.
NCBI— PubMed—New methods for delivery of antifungal agents; Meunier F; http://www.ncbi.nlm.nih.gov/entrez/query.fcgi?cmd_Retrieve&db=PubMed&List_uids-26.
NCBI—PubMed—Improved diagnosis and prognosis of mucormycosis. A clinicopathologic study of 33 cases; Palfrey NA; http://www.ncbi.nlm.nih.gov/entrez/query.fcgi?cmd_Retrieve&db=PubMed&List_uids-39.
NCBI—PubMed—Aspergillosis of themaxillary sinuses in otherwise healthy patients; Meikle D, Yarington CT Hr, Winterbauer RH; http://www.ncbi.nlm.nih.gov/entrez/query.fcgi?cmd_Retrieve&db=PubMed&List_uids-40.
NCBI—PubMed—Primary pituitary aspergillosis responding to transsphenoidal surgery and combined therapy with amphotericin-B and 5-fluorcytosine: case report.
NCBI—PubMed—Patient survival factors in paranasal sinus mucormycosis; Bletzer A, Lawson W, Meyers BR, Biller HF; http://www.ncbi.nlm.nih.gov/entrez/query.fcgi?cmd_Retrieve&db=PubMed&List_uids-73.
Invasive aspergillus rhinosinusitis in patients with acute leukemia (Mar.-Apr. 13, 1991) http://www.ncbi/nlm.nih.gov/entrez/query.fcgi?cmd_Retrieve&db=PubMed&List_uids-19.
Efficacy of Sch39304 in murine cyptococcosis (Aug. 1989) http://www.ncbi.nlm.nih.gov/entrez/query.fcgi?cmd_Retrieve&db=PubMed&List_uids-25.
Lacy, C. et al., 1999-2000 Drug Information Handbook, Lexi-Comp, Inc., Cleveland, 1999, pp. 112-114.
Lacy, C. et al., Drug Information Handbook, Lexi-Comp, Inc., Cleveland, 1999, pp. 445-446.
FLONASE® from the online Physician's Desk Reference (PDR®)—accessed Dec. 1, 2007.
"BECONASE AQ®" from the online Physician's Desk Reference (PDR®)—accessed Nov. 19, 2007.
Chervinsky, P., "Clinical Review of Once-Daily Beclomethasone Dipropionate for Seasonal Allergic Rhinitis", Clinical Therapeutics, 1996, 18(5), pp. 790-796.
Lacy et al., 1999-2000 Drug Information Handbook, Lexi-Comp, Inc., Aug. 21, 1999, 26-28, 2.
Walker, Management of Allergic Rhinitis, Nursing Times, Aug. 21, 2003, 99(23).
Humuy et al., Topical Antiviral Agents for Herpes Simplex Virus Infections, Drugs Today, Aug. 21, 1998, 34(12).

(56) References Cited

OTHER PUBLICATIONS

Vippagunta et al., Crystalline Solids, Advanced Drug Delivery Reviews, Aug. 21, 2001, 3-26, 48.
Lacy et al., 1999-2000 Drug Information Handbook, Lexi-Comp, Inc., 1999, pp. 561-563 and 568-569.
Hebrecht et al., "Voriconazole versus amphotericin B for primary therapy of invasive aspergillosis", N.Eng. J. Med., 2002, 347(6), pp. 408-415.
Bernstein, I. L., *Is the Use of Benzalkonium Chloride as a Preservative for Nasal Formulations a Safety Concern? A Cautionary Note Based on Compromised Mucociliary Transport*, J. Allergy Clin. Immunol., 105(1), Jan. 2000, pp. 39-44.
Office Action dated Jul. 12, 2010, and issued in connection with corresponding Canadian Application No. 2,522,294 (Our Ref: 340938).
Office Action dated Aug. 6, 2010, and issued in connection with corresponding U.S. Appl. No. 10/657,550 (Our Ref: 277062).
Parikh, A., et al.; Topical corticosteroids in chronic rhinosinusitis: a randomized, double-blind, placebo-controlled trial using fluticasone propionate aqueous nasal spray; Rhinology, 39; 2001; pp. 75-79.
Office Action for Japanese Application No. 2006-504903 dated Aug. 4, 2010.
Office Action for Japanese Application No. 2006-504901 dated Aug. 4, 2010.
Office Action for Japanese Application No. 2006-504902 dated Aug. 4, 2010.
Office Action for Japanese Application No. 2006-516000 dated Sep. 8, 2010.
Office Action for Australian Application No. 2004229148; dated Jan. 30, 2009.
Office Action for Australian Application No. 2004229148; dated Feb. 18, 2010.
Office Action for Canadian Application No. 2,522,292; dated Jul. 20, 2010.
Office Action for Chinese Application No. 200480016646.3; dated Jul. 20, 2007.
Office Action for Chinese Application No. 200480016646.3; dated Sep. 4, 2009.
Office Action for Chinese Application No. 200480016646.3; dated Jul. 28, 2010.
Office Action for Chinese Application No. 200480016646.3; dated Mar. 23, 2011.
Office Action for Chinese Application No. 201110287403.5; dated Sep. 9, 2012.
Office Action for Chinese Application No. 201110287403.5; dated Mar. 21, 2013.
Office Action for Chinese Application No. 201110287403.5; dated Jul. 1, 2013.
Office Action for European Application No. 04 724 015.5; dated Apr. 30, 2009.
Office Action for European Application No. 04 724 015.5; dated Sep. 18, 2012.
Office Action for Indian Application No. 1851/KOLNP/2005; dated Dec. 29, 2009.
Office Action for Indian Application No. 1851/KOLNP/2005; dated Jul. 16, 2010.
Office Action for Indian Application No. 1851/KOLNP/2005; dated Apr. 23, 2014.
Office Action for Korean Application No. 2005-7019609; dated Apr. 7, 2011.
Office Action for Korean Application No. 2005-7019609; dated Dec. 23, 2011.
Office Action for Korean Application No. 2005-7019609; dated May 11, 2012.
Office Action for Korean Application No. 2005-7019609; dated Jan. 25, 2013.
Office Action for Korean Application No. 2005-7019609; dated Apr. 19, 2013.
Office Action for Korean Application No. 2005-7019609; dated Jun. 21, 2013.
Office Action for Mexican Application No. PA/a/2005/011107; dated Oct. 16, 2011.
Office Action for Mexican Application No. PA/a/2005/011107; dated Feb. 13, 2012.
Office Action for Polish Application No. P377854; dated Nov. 28, 2008.
Office Action for Polish Application No. P377854; dated Oct. 18, 2011.
Office Action for Polish Application No. P377854; dated Feb. 13, 2013.
Office Action for Russian Application No. 2005 135 335; dated Feb. 20, 2008.
Office Action for Russian Application No. 2005 135 335; dated Aug. 19, 2008.
Office Action for Russian Application No. 2005 135 335; dated Feb. 26, 2009.
Office Action for Russian Application No. 2005 135 335; dated Jul. 21, 2009.
Office Action for Singaporean Application No. 200506602-2; dated Jun. 15, 2006.
Office Action for Singaporean Application No. 200506602-2; dated Feb. 22, 2007.
Office Action for Singaporean Application No. 200506602-2; dated Jan. 11, 2008.
Office Action for Singaporean Application No. 200506602-2; dated Apr. 15, 2010.
"*A 8 d—Particle Size Distribution by Laser (Malvern)*;" GEA Niro; retrieved on Feb. 27, 2012 from <http://www.niro.com/cmsdoc.nsf/webdoc/ndkw6u9by4/>.
"*A Guidebook to Particle Size Analysis*;" Horiba Scientific; dated 2010.
International Preliminary Report on Patentability for Application No. PCT/EP2004/003314; dated Oct. 21, 2005.
International Search Report and Written Opinion for Application No. PCT/EP2004/003314; dated Sep. 1, 2004.
International Preliminary Report on Patentability for Application No. PCT/EP2004/003315; dated Oct. 21, 2005.
International Search Report and Written Opinion for Application No. PCT/EP2004/003315; dated Aug. 23, 2004.
International Preliminary Report on Patentability for Application No. PCT/EP2004/003316; dated Oct. 21, 2005.
International Search Report and Written Opinion for Application No. PCT/EP2004/003316; dated Aug. 30, 2004.
Office Action for Australian Application No. 2004229147; dated Oct. 17, 2008.
Office Action for Australian Application No. 2004229147; dated Feb. 24, 2010.
Office Action for Australian Application No. 2004229147; dated May 25, 2010.
Office Action for Australian Application No. 2004229149; dated Nov. 4, 2008.
Office Action for Australian Application No. 2004229149; dated Jan. 29, 2010.
Office Action for Australian Application No. 2010203026; dated Jun. 21, 2012.
Office Action for Canadian Application No. 2,522,291; dated Jul. 19, 2010.
Office Action for Canadian Application No. 2,522,294; dated Jun. 15, 2011.
Office Action for Canadian Application No. 2,522,294; dated Aug. 21, 2012.
Office Action for Canadian Application No. 2,522,294; dated Jan. 17, 2013.
Office Action for Chinese Application No. 200480016645.9; dated Sep. 7, 2007.
Office Action for Chinese Application No. 200480016645.9; dated Sep. 18, 2009.
Office Action for Chinese Application No. 200480010070.X; dated Mar. 23, 2007.
Office Action for Chinese Application No. 200480010070.X; dated Aug. 28, 2009.
Office Action for Chinese Application No. 200480010070.X; dated Dec. 18, 2009.

(56) References Cited

OTHER PUBLICATIONS

Office Action for Chinese Application No. 200480010070.X; dated Jul. 16, 2010.
Office Action for Chinese Application No. 200480010070.X; dated Aug. 4, 2011.
Office Action for Chinese Application No. 200480010070.X; dated Nov. 5, 2012.
Office Action for Chinese Application No. 200480010070.X; dated Mar. 20, 2013.
Office Action for European Application No. 04 723 993.4; dated Apr. 30, 2009.
Office Action for European Application No. 04 723 993.4; dated Sep. 18, 2012.
Office Action for European Application No. 04 724 018.9; dated Apr. 30, 2009.
Office Action for European Application No. 04 724 018.9; dated Sep. 18, 2012.
Office Action for Indian Application No. 1850/KOLNP/2005-D; dated Nov. 4, 2008.
Office Action for Japanese Application No. 2006-504901; dated Apr. 6, 2011.
Office Action for Japanese Application No. 2006-504901; dated Aug. 8, 2011.
Office Action for Japanese Application No. 2006-504901; dated Oct. 1, 2013.
Office Action for Korean Application No. 2005-7019610; dated Apr. 7, 2011.
Office Action for Korean Application No. 2005-7019610; dated Dec. 23, 2011.
Office Action for Korean Application No. 2005-7019610; dated May 11, 2012.
Office Action for Korean Application No. 2005-7019610; dated May 21, 2013.
Office Action for Korean Application No. 2005-7019610; dated Jun. 21, 2013.
Office Action for Korean Application No. 2005-7019698; dated Apr. 7, 2011.
Office Action for Korean Application No. 2005-7019698; dated Dec. 23, 2011.
Office Action for Korean Application No. 2005-7019698; dated May 11, 2012.
Office Action for Korean Application No. 2005-7019698; dated Jan. 25, 2013.
Office Action for Korean Application No. 2005-7019698; dated Apr. 19, 2013.
Office Action for Korean Application No. 2005-7019698; dated May 21, 2013.
Office Action for Korean Application No. 2005-7019698; dated Jun. 21, 2013.
Office Action for Philippines Application No. 1-2005-501687 dated Jul. 14, 2009.
Office Action for Philippines Application No. 1-2005-501687 dated Jun. 23, 2010.
Office Action for Polish Application No. P377855; dated Jan. 17, 2011.
Office Action for Polish Application No. P377855; dated May 18, 2011.
Office Action for Polish Application No. P377855; dated Oct. 18, 2011.
Office Action for Polish Application No. P377855; dated Nov. 24, 2011.
Office Action for Polish Application No. P377855; dated Feb. 15, 2013.
Office Action for Polish Application No. P377855; dated Jan. 16, 2014.
Office Action for Russian Application No. 2005 135 333; dated Feb. 18, 2008.
Office Action for Russian Application No. 2005 135 333; dated Jul. 3, 2008.
Office Action for Russian Application No. 2005 135 333 dated Jun. 15, 2010.
Office Action for Russian Application No. 2005 135 333; dated Jul. 15, 2010.
Office Action for Singaporean Application No. 200506603-0; dated Jul. 26, 2006.
Office Action for Singaporean Application No. 200506603-0; dated Mar. 15, 2007.
Office Action for U.S. Appl. No. 10/414,756; dated Dec. 19, 2008.
Office Action for U.S. Appl. No. 10/414,756; dated Jul. 12, 2010.
Office Action for U.S. Appl. No. 11/078,263; dated Jan. 6, 2009.
Office Action for U.S. Appl. No. 11/078,263; dated Jan. 21, 2010.
Office Action for U.S. Appl. No. 11/078,263; dated Jul. 8, 2010.
Office Action for U.S. Appl. No. 11/250,220; dated Feb. 28, 2006.
Office Action for U.S. Appl. No. 11/250,220; dated Dec. 6, 2006.
Office Action for U.S. Appl. No. 11/250,220; dated May 21, 2007.
Office Action for U.S. Appl. No. 11/250,220; dated Feb. 8, 2008.
Office Action for U.S. Appl. No. 11/250,256; dated Feb. 28, 2006.
Office Action for U.S. Appl. No. 11/250,256; dated Sep. 28, 2006.
Office Action for U.S. Appl. No. 11/250,256; dated Nov. 28, 2007.
Office Action for U.S. Appl. No. 11/250,925; dated Mar. 10, 2006.
Office Action for U.S. Appl. No. 11/250,925; dated Sep. 13, 2006.
Office Action for U.S. Appl. No. 11/250,925; dated Apr. 25, 2007.
Office Action for U.S. Appl. No. 11/250,925; dated Dec. 5, 2007.
Office Action for U.S. Appl. No. 11/250,925; dated Aug. 11, 2008.
Office Action for U.S. Appl. No. 11/250,925; dated Sep. 9, 2009.
Office Action for U.S. Appl. No. 11/250,925; dated Apr. 8, 2010.
Office Action for U.S. Appl. No. 11/931,380; dated May 8, 2013.
Office Action for U.S. Appl. No. 11/931,380; dated May 2, 2014.
Office Action for U.S. Appl. No. 11/931,424; dated May 23, 2011.
Office Action for U.S. Appl. No. 11/931,484; dated Dec. 2, 2008.
Office Action for U.S. Appl. No. 11/931,484; dated Mar. 4, 2010.
Office Action for U.S. Appl. No. 11/931,484; dated May 3, 2012.
Office Action for U.S. Appl. No. 11/931,484; dated Apr. 25, 2013.
Office Action for U.S. Appl. No. 13/368,873; dated Feb. 10, 2014.
The John Hopkins Sinus Center, "Rhinosinusitis," <http://www.hopkinsmedicine.org/sinus/sinus_conditions/rhinosinusitis.html> © dated 2008; pp. 1-2.
"*Vancenase AQ*;" Drugs.com; retrieved on May 7, 2014 from <http://www.drugs.com/mtm/vancenase-aq.html>.
Dyson, G. et al., *Chemistry of Synthetic Drugs*, "Mir", 1964, pp. 12-16.
Vervloet et al., "Intranasal Fluticasone Once Daily Compared with Once-daily Cetirizine in the Treatment of Seasonal Allergic Rhinitis: Results of a Multicentre, Double-Blind Study," Clinical Drug Investigation, 1997, 13(6), pp. 291-298.
Waligorski et al., Raman Chemical Imaging of Complex Pharmaceutical Products. [online], [retrieved on Jan. 4, 2010]. Retrieved from the internet <http://www.chemimage.com/docs/posters/Pharmaceutical/RCI_of_Complex_Pharmaceutical_Products.pdf>.
Comparison of Drug Particle Sizing of Innovator and Generic Nasal Spray Formulations Based on Raman Chemical Imaging. [online], [retrieved on Jan. 4, 2010]. Retrieved from the internet <http://www.chemimage.com/docs/white-papers/CI_ISPS_White_Paper.pdf>.
Merriam-Webster's Collegiate Dictionary, 10$^{th}$ edition, Merriam-Webster Incorporated: Springfield, Massachusetts, 1993 p. 311.
Office Action for Russian Application No. 2005 135 333 dated Dec. 17, 2008.
Office Action for Russion Application No. 2005 135 332 dated Sep. 29, 2008.
Office Action for Russian Application No. 2005 135 332 dated Dec. 21, 2007.
Encyclopaedia of Medical Terms, edited by the member of the Russian Academy of Medical Sciences V.A. Pokrovsky, second edition, M., "Medicina", 2001, pp. 697-698.
Office Action for U.S. Appl. No. 10/657,550 dated Apr. 23, 2007.
Office Action for U.S. Appl. No. 10/657,550 dated Dec. 5, 2007.
Office Action for U.S. Appl. No. 10/657,550 dated Aug. 4, 2008.
Office Action for U.S. Appl. No. 10/657,550 dated Apr. 13, 2009.
Office Action for U.S. Appl. No. 10/657,550 dated Nov. 16, 2009.
Office Action for U.S. Appl. No. 10/657,550 dated Mar. 3, 2010.
Office Action for U.S. Appl. No. 10/657,550 dated May 9, 2013.

(56) References Cited

OTHER PUBLICATIONS

Office Action for U.S. Appl. No. 10/657,550 dated Sep. 18, 2013.
Office Action for U.S. Appl. No. 11/931,380 dated Dec. 12, 2008.
Office Action for U.S. Appl. No. 11/931,380 dated Jan. 25, 2010.
Office Action for U.S. Appl. No. 11/931,380 dated Sep. 24, 2010.
Office Action for U.S. Appl. No. 11/931,380 dated May 23, 2011.
Office Action for U.S. Appl. No. 11/931,380 dated May 8, 2013.
Office Action for U.S. Appl. No. 11/931,484 dated Dec. 2, 2008.
Office Action for U.S. Appl. No. 11/931,484 dated Sep. 10, 2009.
Office Action for U.S. Appl. No. 11/931,484 dated Mar. 4, 2010.
Office Action for U.S. Appl. No. 11/931,484 dated Aug. 10, 2010.
Office Action for U.S. Appl. No. 11/931,484 dated Jun. 23, 2011.
Office Action for U.S. Appl. No. 11/931,484 dated Nov. 30, 2011.
Office Action for U.S. Appl. No. 11/931,484 dated May 3, 2012.
Office Action for U.S. Appl. No. 11/931,484 dated Nov. 19, 2012.
Office Action for U.S. Appl. No. 11/931,484 dated Apr. 25, 2013.
Office Action for U.S. Appl. No. 11/931,484 dated May 16, 2013.
Notice of Allowance for U.S. Appl. No. 11/931,484 dated Oct. 4, 2013.
Office Action for European Application No. 04 723 993.4 dated Dec. 1, 2014.
Office Action for European Application No. 04 723 993.4 dated Sep. 8, 2015.
Office Action for European Application No. 04 724 015.5 dated Oct. 16, 2014.
Office Action for European Application No. 04 724 015.5 dated Jun. 9, 2015.
Office Action for European Application No. 04 724 018.9 dated Oct. 16, 2014.
Office Action for European Application No. 04 724 018.9 dated Jun. 9, 2015.
Decision granting patent for Indian Patent Application No. 1851/KOLNP/2005 dated Aug. 26, 2014.
Office Action for Indonesian Application No. WO0200502776 dated Mar. 18, 2015.
Office Action for Polish Application No. P377854 dated Apr. 8, 2014.
Office Action for U.S. Appl. No. 10/657,550 dated Feb. 12, 2014.
Notice of Allowance from U.S. Appl. No. 10/657,550, dated Aug. 11, 2014.
Office Action for U.S. Appl. No. 13/368,873 dated Oct. 29, 2014.
Notice of Allowance for U.S. Appl. No. 13/368,873 dated Jul. 7, 2015.
Office Action for U.S. Appl. No. 11/931,380 dated Nov. 5, 2013.
Office Action for U.S. Appl. No. 11/931,380 dated Dec. 2, 2014.
Office Action for U.S. Appl. No. 11/931,380 dated Jul. 23, 2015.
Office Action for U.S. Appl. No. 11/931,380 dated Nov. 17, 2015.
Office Action for U.S. Appl. No. 11/931,380 dated Mar. 23, 2016.
Russian Office Action for Russian Application No. 2005 135 333.
USFDA—Drug Approval Package—Flonase (Fluticasone Propionate) Nasal Spray.
Steckel, H., et al., "In Vitro Characterization of Jet-Milled and In-Situ-Micronized Fluticasone-17-Propionate," International Journal of Pharmaceutics, 2003, vol. 258, pp. 65-75.
Steckel, H., et al., "Metered-Dose Inhaler Formulation of Fluticasone-17-Propionate Micronized with Supercritical Carbon Dioxide Using the Alternative Propellant HFA-227," International Journal of Pharmaceutics, 1998, vol. 173, pp. 25-33.
Denyer, S., "Pharmaceutical Properties of Fluticasone Propionate Nasal Drops: A New Formulation," Allergy, 1999, vol. 54, pp. 17-20.
Mygind, N., et al., "Simultaneous Treatment of Rhinitis and Asthma by Nasal Inhalation of Corticosteroid From a Spacer," Allergy, 1999, vol. 54, pp. 132-135.

\* cited by examiner

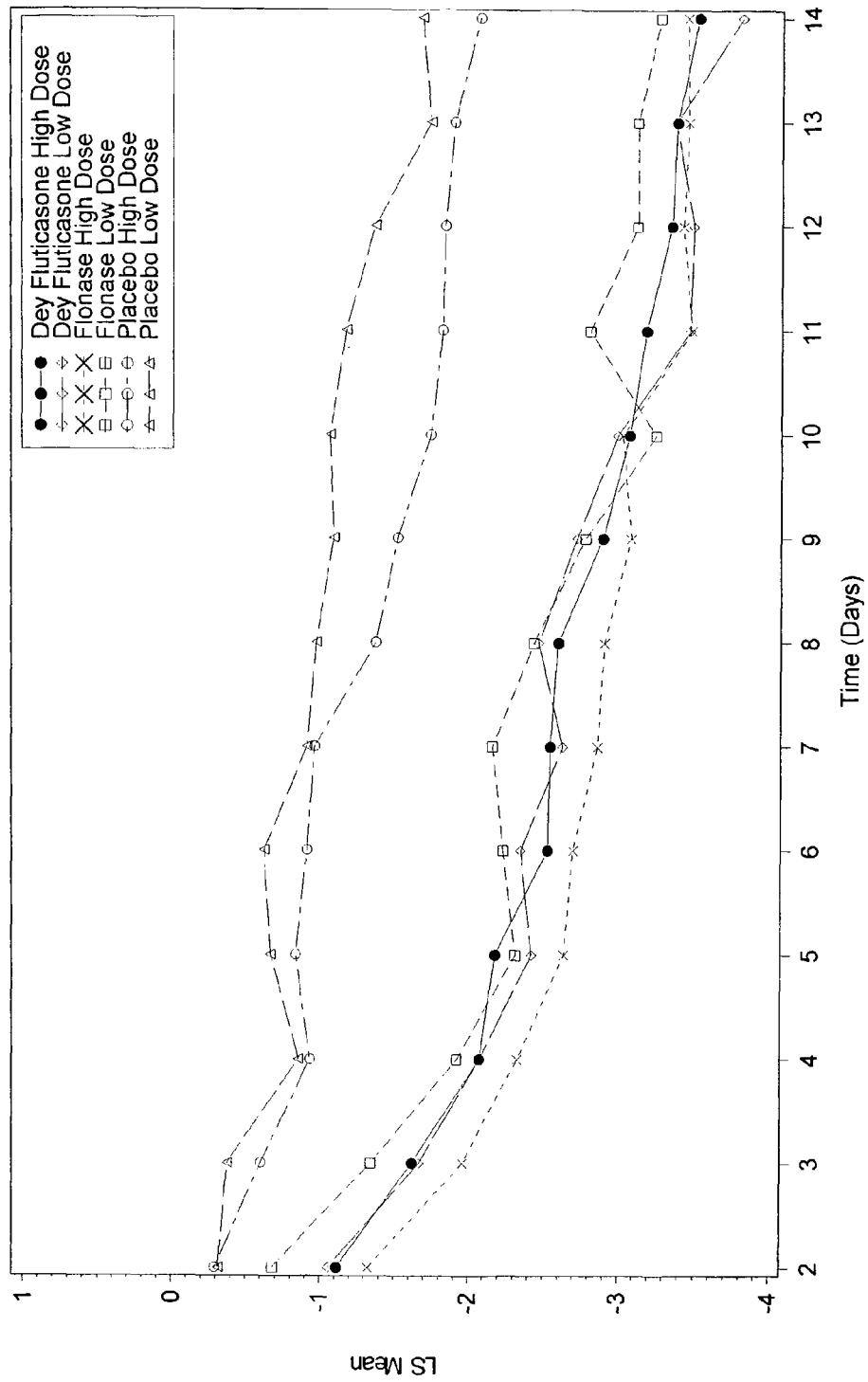

NASAL PHARMACEUTICAL FORMULATIONS AND METHODS OF USING THE SAME

I. FIELD OF THE INVENTION

The present invention is directed to nasal pharmaceutical formulations comprising a drug substance having a specific particle size distribution profile. Such profile provides increased bioavailability, increased efficacy or prolonged therapeutic effect of the drug substance when administered intranasally. In an alternative embodiment, formulations of the present invention comprise a fluticasone or a pharmaceutically acceptable derivative thereof having a specific particle size distribution profile. The formulation may be provided as an aqueous suspension suitable for intranasal administration to a subject in need thereof.

II. BACKGROUND OF THE INVENTION

It is known that the particle size of a drug substance affects bioavailability of the drug and efficacy. Methods of making finely divided drugs have been studied and efforts have been made to control the size and size range of drug particles in pharmaceutical compositions. However, the prior art does not disclose drug substances having specific particle size distribution profiles which provide increased bioavailability, increased efficacy or prolonged therapeutic effect of the drug when administered intranasally.

It is known that inhaled corticosteroids are one of the most effective anti-inflammatory medications used in the treatment of respiratory disorders or diseases characterized by inflammation. One such corticosteroid, fluticasone propionate (FP), is particularly useful in the treatment or prophylaxis of seasonal or perennial rhinitis and is also indicated for the relief of one or more symptoms associated with seasonal or perennial allergic and non-allergic (vasomotor) rhinitis. Rhinitis is a reaction that occurs in the eyes, nose and throat when airborne irritants, for example, trigger the release of histamine. Histamine causes inflammation and fluid production in the fragile linings of nasal passages, sinuses and eyelids. Use of corticosteroids such as fluticasone can cause partial or whole relief from rhinitis-related symptoms such as sneezing, congestion, runny nose, itchy nose, throat eyes and ears. Use of fluticasone can also delay the recurrence of nasal polyps in individuals who have undergone nasal polyopectomy. In those polyps that do recur, fluticasone can suppress the polyp's growth increase in size.

Like most corticosteroids and other drug substances, FP is very slightly soluble in water. When such drug substances are administered intranasally, they are typically suspended in an aqueous solution. However, when these substances are administered intranasally via a conventional nasal spray, less than optimal amounts of drug substance is absorbed by the nasal mucosa (the target tissue), with the remainder being swallowed or expelled from the nasal cavity. In some instances, particles which are not sufficiently small are eliminated from the gastrointestinal tract before being disposed onto the target area. The inability to administer optimal amounts of a drug substance results in reduced bioavailability and efficacy of that drug substance.

III. SUMMARY OF THE INVENTION

The present invention is directed to a nasal pharmaceutical formulation comprising a drug substance having a specific particle size distribution profile which provides increased bioavailability, increased efficacy or prolonged therapeutic effect of the drug substance when administered intranasally. Specifically, in one alternative embodiment, the formulation of the present invention comprises a drug substance (e.g., active ingredient) having the following particle size distribution profile: about 10% of the drug substance particles have a particle size of about 0.90 microns; about than 25% of the drug substance particles have a particle size of less than 1.6 microns; about 50% of the drug substance particles have a particle size of less than 3.2 microns; about 75% of the drug substance particles have a particle size of less than 6.10 microns; about 90% of the drug substance particles have a particle size of less than 10.0 microns. In one alternative embodiment, the drug substance is a corticoid steroid, preferably fluticasone or a pharmaceutically acceptable derivative thereof.

IV. FIGURES

FIG. 3 shows the change from baseline in AM reflective TNSS over time in the PP population over a 14 day study period.

V. DETAILED DESCRIPTION OF THE INVENTION

Figure 1:
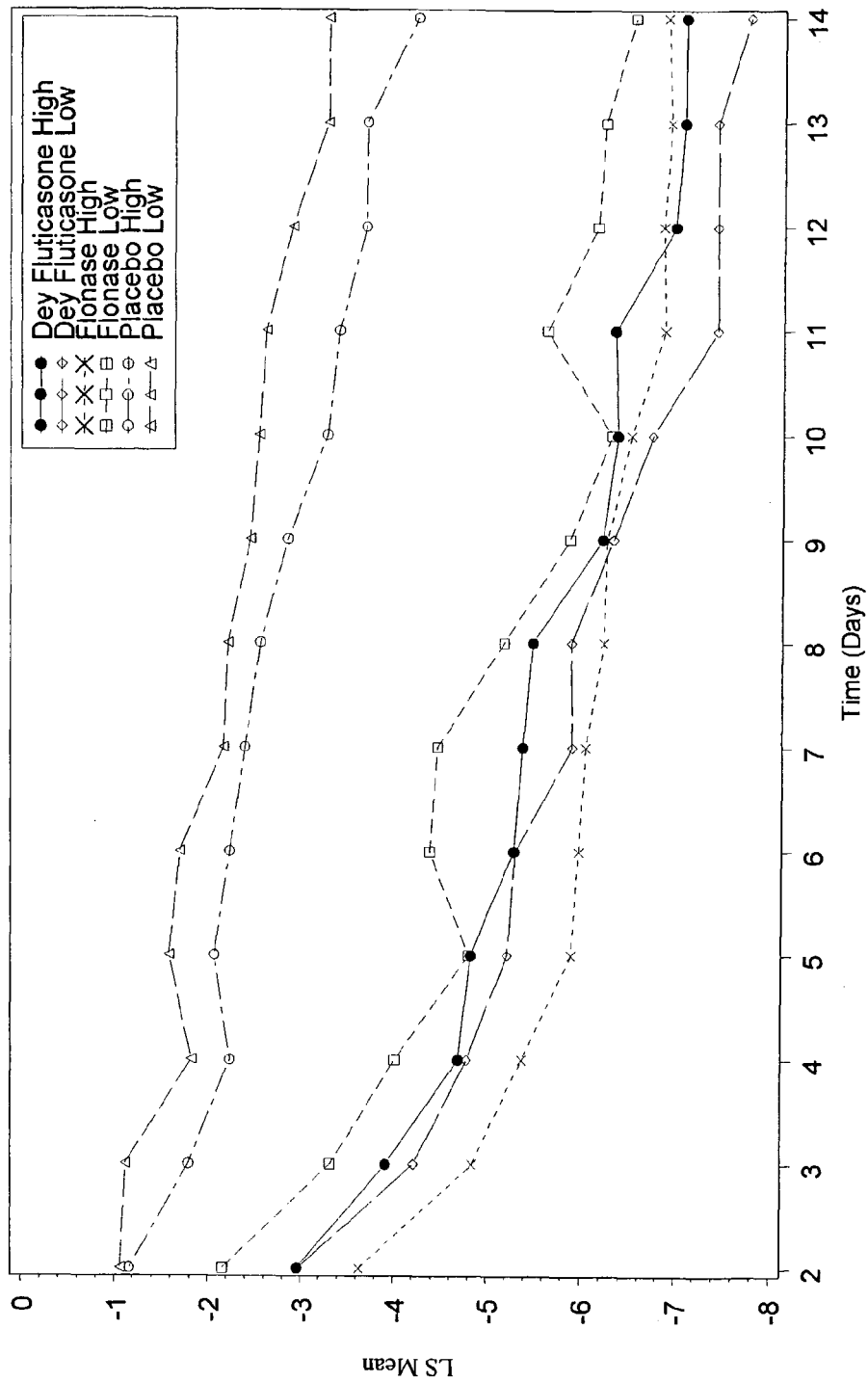
FIG. 1 shows the change from baseline in AM and PM reflective TNSS over time in the ITT population over a 14 day study period.

The formulations provided herein are used for treating, preventing and/or ameliorating one or more symptoms of a medical condition, disorder or disease. As used herein, treatment means any manner in which one or more of the symptoms of the condition, disorder or disease are ameliorated or otherwise beneficially altered. Treatment also encompasses any pharmaceutical or medicinal use of the formulations herein. As used herein, amelioration of the symptoms of a particular disorder by administration of a particular formulation refers to any lessening, whether permanent or temporary, lasting or transient that can be attributed to or associated with administration of the formulation. As used herein, a "therapeutic effective amount" means a sufficient amount of drug substance to treat, prevent and/or ameliorate one or more symptoms of a medical condition, disorder or disease. It also may include a safe and tolerable amount of drug substance, as based on industry and/or regulatory standards.

In one alternative embodiment, the formulations provided herein are used for treating, preventing and/or ameliorating one or more symptoms of a respiratory disorder in an individual. In another alternative embodiment, the present invention provides a formulation for the treatment, prophylaxis and/or amelioration of one or more symptoms of rhinitis or other related disorders, wherein the formulation comprises one or more corticosteroids having a specific particle size distribution profile. In an alternative embodiment, the drug substance is fluticasone or a pharmaceutically acceptable derivative thereof. Preferably, the drug substance is fluticasone propionate. Surprisingly, it has been found that a drug substance having the present particle size distribution profiles, when administered intranasally to a subject in need thereof, provides increased bioavailability of the drug substance, as well as increased and prolonged efficacy when compared to conventional formulations containing the same drug substance. Drug substances for use herein include any pharmaceutical compound having the present particle size distribution profile and capable of treating, preventing and/or amelioration one or more symptoms of a medical condition, disorder or disease when such substance is administered intranasally to a subject in need thereof.

Mode of Administration

The present formulations may be packaged for administration in any conventional manner, preferably in a nasal applicator, and preferably in such a way as to deliver a fixed dose of drug substance (e.g., active ingredient). However, the present formulations may be administered via a nasal application in such a way as to deliver a non-fixed dose of drug substance. Spray Administration containers for various types of nasal formulations have been known in the past and substantially all will be equally suitable for the present formulations, considering of course that the materials from which the container is made is compatible with the formulations. The medium containing the drug substance and other appropriate ingredients may be contained in a small bottle or similar container, from which it can be dispersed as a mist to be directed into each nostril. Using ambient air as the propelling agent, one may have the bottle made of a flexible plastic, so that merely squeezing the bottle's sides impels the spray out through the nozzle into the nasal cavity. Air may also be the propelling agent for a pump sprayer, in which the user manipulates a small pump button which pumps air into the container and causes the liquid spray to be emitted on the return stroke. Alternatively, the bottle can be pressurized with a gas which is inert to the user and to the ingredients of the solution. The gas may be dissolved under pressure in the container or may be generated by dissolution or reaction of a solid material which forms the gas as a product of dissolution or as a reaction product. Typical gases which can be used include nitrogen, argon, and carbon dioxide. Also, when the formulation is administered as a spray or aerosol, the formulation may be contained in a pressurized container with a liquid propellant including, but not limited to dicholorodifluoro methane or chlorotrifluoro ethylene, among other propellants.

In another alternative embodiment, for administration as a spray, the present formulations may be placed in an appropriate atomizing device, e.g. in a pump-atomiser or the like. The atomizing device may be provided with appropriate means for delivery of aqueous spray to the naris. Preferably, it is provided with means ensuring delivery of a substantially fixed volume of composition/actuation (i.e. per spray-unit). In one embodiment, the device administers a metered dosage. The spray composition may be suspended or dissolved in a liquid propellant. Stabilizing and/or suspending agents and/or co-solvents may be present. In other embodiments herein, the formulation of the present invention is suitable for administration intranasally via a metered-dose spray pump to a subject in need thereof. In this respect, the formulation of the present invention may be pre-packaged in a metered-dose spray pump bottle, or metering atomizing pump.

In another alternative embodiment, the formulations of the present invention may be administered into the nose in the form of drops, or any other method which results in topical application to the nasal mucosa. The form of dosage for intranasal administration may include solutions, suspensions or emulsions of the active compound in a liquid carrier in the form of nose drops. Suitable liquid carriers include water, propylene glycol and other pharmaceutically acceptable alcohols. For administration in drop form formulations may suitably be put in a container provided e.g. with a conventional dropper/closure device, e.g. comprising a pipette or the like, preferably delivering a substantially fixed volume of composition/drop. The dosage forms may be sterilized, as required. The dosage forms may also contain adjuvants such as preservatives, stabilizers, emulsifiers or suspending agents, wetting agents, salts for varying the osmotic pressure or buffers, as required.

In another alternative embodiment, the present formulations may be administered in the form of a powder. For example, a powdery nasal composition can be directly used as a powder for a unit dosage form. If desired, the powder can be filled in capsules such as hard gelatine capsules. The contents of the capsule or single dose device may be administered using e.g. an insufflator. Preferably, it is provided with means ensuring dosing of a substantially fixed amount of composition/actuation.

Drug Substance

The present invention is directed to formulations for the treatment, prophylaxis, or amelioration of one or more symptoms of a condition, disorder or disease. In alternative embodiment, the present invention is directed to formulations for the treatment, prophylaxis, or amelioration of one or more symptoms of rhinitis or any other respiratory disorder. For example, the formulations disclosed herein are useful for the treatment of seasonal allergic rhinitis (e.g., hay fever) or perennial allergic and nonallergic (vasomotor) rhinitis.

Drug substances suitable for use in the present formulations include any pharmaceutical-acceptable compound company or any of its derivatives including, but not limited to, any salts, esters, enol, esters, enol esters, acids, bases, solvates or hydrates thereof. Such derivatives may be prepared by those of skill in the art using known methods for such derivatization. Further, the drug substances for use in the formulations and methods provided herein include those compounds comprising chiral centers of either the (R) or (S) configuration, or a mixture thereof (e.g., racemate). Thus, the drug substances for use in the compositions provided herein include enantiomerically pure compounds, or stereoisomeric or diastereomeric mixtures thereof. It is to be understood that the chiral centers of the drug substances provided herein may undergo epimerization in vivo. Thus, one of skill in the art will recognize that administration of a drug substance in its (R) form is equivalent, for compounds that undergo epimerization in vivo, to administration of the compound in its (S) form.

Drug substances suitable for use in the present formulations include, but are not limited to, corticosteroids, such as fluticasone and any of its pharmaceutically acceptable derivatives. As used herein, pharmaceutically acceptable derivatives of a fluticasone include any salts, esters, enol ethers, enol esters, acids, bases, solvates or hydrates thereof. Such derivatives may be prepared by those of skill in the art using known methods for such derivatization.

Preferably, the drug substance of the present formulations is fluticasone propionate. Fluticasone propionate is a synthetic corticosteroid and has the empirical formulat $C_{25}H_{31}F_3O_5S$. It has the chemical name S-(fluromethyl)6α, 9-difluoro-11β-17-dihydroxy-16α-methyl-3-oxoandrosta-1, 4-diene-17β-carbothioate, 17-propionate and the following structural formula:

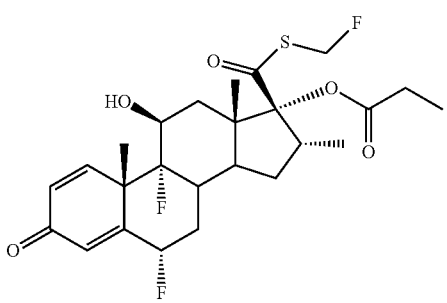

Fluticasone propionate is a white to off-white powder with a molecular weight of 500.6 and is practically insoluble in water, freely soluble in dimethyl sulfoxide and dimethylformamide, and slightly soluble in methanol and 95% ethanol.

Particle Size Distribution Profile

The formulations of the present invention may comprise a cocorticosteroid (e.g., beclometasone diproprionate) having the following particle size distribution profile: about 10% or less of the drug substance particles have a particle size of less than 0.90 microns; about 25% or less of the drug substance particles have a particle size of less than 1.6 microns; about 50% or less of the drug substance particles have a particle size of less than 3.2 microns; about 75% or less of the drug substance particles have a particle size of less than 6.10 microns; about 90% or less of the drug substance particles have a particle size of less than 10 microns. Surprisingly, it has been discovered that formulations containing a cocorticosteroid (e.g., fluticasone diproprionate) having a particle size distribution profile falling within the above ranges provide increased bioavailability over conventional formulations when administered via the intranasal route to a subject in need thereof, as well as increased and prolonged drug efficacy.

As used herein, particle size refers to an average particle size as measured by conventional particle size measuring techniques well known to those skilled in the art, such as sedimentation field flow fractionation, photon correlation spectroscopy, or disk centrifugation, among other techniques.

In an alternative embodiment, the formulation of the present invention comprises a drug substance having the following particle size distribution profile: about 10% of the drug substance particles have a particle size of less than 0.70 microns; about 25% of the drug substance particles have a particle size of less than 1.30 microns; about 50% of the drug substance particles have a particle size of less than 2.5 microns; about 75% of the drug substance particles have a particle size of less than 4.0 microns; about 90% of the drug substance particles have a particle size of less than 6.0 microns; and greater than 90% or about 100% of the drug substance particles have a particle size of less than 10 microns. Preferably, the drug substance is fluticasone propionate.

The formulations of the present invention may also comprise a drug substance having the following particle size distribution profile: about 10% of the drug substance particles have a particle size less than 0.90, 0.75, 0.70, 0.60, 0.55, 0.50, 0.40, 0.35, 0.30, 0.25, 0.20, 0.15, 0.10, or 0.05 microns; about 25% of the drug substance particles have a particle size less than 1.6, 1.5, 1.45, 1.40, 1.35, 1.30, 1.25, 1.20, 1.15, 1.10, 1.05, 1.0, 0.95, 0.90, 0.85, 0.80, 0.75, 0.70, 0.65, 0.60, 0.55, 0.50, 0.45, 0.40, 0.35, 0.30, 0.25, 0.20, 0.15, or 0.10 microns; about 50% of the drug substance particles have a particle size less than 3.2, 3.0, 2.5, 2.4, 2.3, 2.2, 2.1, 2.0, 1.9, 1.8, 1.7, 1.6, 1.5, 1.4, 1.3, 1.2, 1.1, 0.9, 0.8, 0.7, or 0.6 microns. About 75% of the drug substance particles have a particle size less than 6.0, 5.5, 5.0, 4.5, 4.0, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, or 1.4 microns; about 90% of the drug substance particles have a particle size less than 10, 9, 8, 7, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, or 2.1 microns and greater than 90% or about 100% of the drug substance particles have a particle size less than 10, 9.5, 9.0, 8.5, 8.0, 7.5, 7.0, 6.5, 6.0, 5.5, 5.0, 4.5, or 0.40 microns.

In one preferred embodiment, the formulation of the present invention comprises a drug substance having the following particle size distribution profile: about 10% of the drug substance particles have a particle size less than 0.50 microns; about 25% of the drug substance particles have a particle size less than 0.90 microns; about 50% of the drug substance particles have a particle size less than 1.7 microns; about 75% of the drug substance particles have a particle size less than 3.5 microns; about 90% of the drug substance particles have a particle size less than 5.5 microns.

In another alternative embodiment, the formulation of the present invention comprises a drug substance having the following particle size distribution profile: about 10% of the drug substance particles have a particle size less than 0.40 microns; 25% of the drug substance particles have a particle size less than 0.80 microns; about 50% of the drug substance particles have a particle size less than 1.60 microns; about 75% of the drug substance particles have a particle size less than 3.0 microns; about 90% of the drug substance particles have a particle size less than 5.3 microns.

In another alternative embodiment, greater than 90% or about 100% of the particles have a particle size less than 15 microns, preferably less than 10 microns, more preferably less than 8 microns, most preferably less than 7 microns.

In one alternative embodiment, such aqueous suspension formulations are suitable for direct administration to a subject via the nasal passages and represent an improvement over conventional techniques for administering the drug substances intranasally, particularly fluticasone. Specifically, due to the specific particle size distribution profile of the drug substance, the present formulations provide increased bioavailability of the drug substance as well as increased efficacy and/or prolonged therapeutic effect of the drug substance.

The formulation of the present invention may be provided as an aqueous suspension. As used herein, suspension include, but are not limited to, mixtures of fine, non-settling particles of a solid within a liquid phase. In one embodiment, the formulation of the present invention is an aqueous suspension comprising about 0.005% to about 10% by weight of a drug substance. In alternate embodiment, the drug substance is fluticasone.

In another alternate embodiment, the formulation of the present invention is an aqueous suspension comprising about 0.005% to about 5%, or about 0.01% to about 2.5%, or about 0.01% to about 0.2%, or about 0.01% to about 0.1%, or about 0.1% to about 0.75% by weight of a drug substance. In a preferred embodiment, the formulation is an aqueous suspension comprising about 0.025% to about 1.0% of a drug substance, wherein the drug substance is preferably fluticasone. Even more preferably, the formulation is an aqueous suspension comprising about 0.04% to about 0.06% by weight of a drug substance wherein the drug substance is preferably fluticasone propionate. In a preferred embodiment, the formulation of the present invention is an aqueous suspension comprising about 0.045% by weight of fluticasone propionate, wherein the fluticasone propionate has the following particle size distribution profiles disclosed herein.

In one alternate embodiment, the nasal formulation of the present invention may comprise a preservative, suspending agent, wetting agent, tonicity agent and/or diluent. The formulations provided herein may comprise from about 0.01% to about 90%, or about 0.01% to about 50%, or about 0.01% to about 25%, or about 0.01% to about 10%, or about 0.01% to about 5% of one or more pharmacologically suitable suspending fluids which is physiologically acceptable upon administration intranasally. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in inhaled drugs.

In certain embodiments herein, the formulations of the present invention have a pH of from about 2.0 to about 9.0, preferably about 4.0 to about 7.0, more preferably about 4.0 and about 5.0. Optionally, the formulations of the present invention may contain a pH buffer. Such a buffer may comprise any known pharmaceutically suitable buffers which are physiologically acceptable upon administration intranasally.

Sterility or adequate antimicrobial preservation may be provided as part of the present formulations. Since certain formulations of the present invention are intended to be administered intranasally, it is preferred that they be free of pathogenic organisms. A benefit of a sterile liquid suspension is that it reduces the possibility of introducing contaminants into the individual when the suspension formulation is administered intranasally, thereby reducing the chance of an opportunistic infection. Processes which may be considered for achieving sterility may include any appropriate sterilization steps known in the art. In one embodiment, the drug substance (e.g., fluticasone) is produced under sterile conditions, the micronization is performed in a sterile environment, and the mixing and packaging is conducted under sterile conditions. In alternative embodiment, the formulations of the present invention may be sterile filtered and filled in vials, including unit dose vials providing sterile unit dose formulations which are used in a nasal spray device for example. Each unit dose vial may be sterile and is suitably administered without contaminating other vials or the next dose. In one alternative embodiment, one or more ingredients in the present formulation may be sterilized by steam, gamma radiation or prepared using or mixing sterile steroidal powder and other sterile ingredients where appropriate. Also, the formulations may be prepared and handled under sterile conditions, or may be sterilized before or after packaging.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for inhalation safety, as the treated tissues may be sensitive to irritants. Preservatives suitable for use herein include, but are not limited to, those that protect the solution from contamination with pathogenic particles, including phenylethyl alcohol, benzalkonium chloride or benzoic acid, or benzoates such as sodium benzoate and phenylethyl alcohol. Preferably, the preservative for use in the present formulations is benzalkonium chloride. In certain embodiments, the formulations herein comprise from about 0.001% to about 10.0% w/w of benzalkonium chloride, or from about 0.01% v/w phenylethyl alcohol. Preserving agents may also be present in an amount from about 0.001% to about 1%, preferably about 0.002% to about 0.02%, more preferably 0.02% w/w.

The formulations provided herein may also comprise from about 0.001% to about 90%, or about 0.001% to about 50%, or about 0.001% to about 25%, or about 0.001% to about 10%, or about 0.001% to about 1% of one or more emulsifying agent, wetting agent, or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono-and di-glycerides of fatty acids; mono-and diacetyl-tartaric acid esters of mono-and di-glycerides of fatty acids; mixed acetic and tartaric acid esters of mono-and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract. In certain embodiments herein, the present formulations comprise polysorbate 80, microcrystalline cellulose, carboxymethylcellulose sodium and/or dextrose.

The present formulations may further comprise from about 0.001% to about 90%, or about 0.001% to about 50%, or about 0.001% to about 25%, or about 0.001% to about 10%, or about 0.001% to about 1% of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, or other additives known in the art. Complexing agents include, but are not limited to, ethylenediaminetetraacetic acid (EDTA) or a salt thereof, such as the disodium salts, citric acid, nitrilotriacetic acid and the salts thereof. In another embodiment, particularly in the suspension formulations provided herein, the complexing agent is sodium edetate. In one embodiment, the compositions contain sodium edetate at a concentration of about 0.05 mg/ml to about 0.5 mg/ml, or about 0.1 mg/ml to about 0.2 mg/ml. Also, for example, the formulations of the present invention may comprise from about 0.001% to about 5% by weight of a humectant to inhibit drying of the mucous membrane and to prevent irritation. Any of a variety of pharmaceutically-acceptable humectants can be employed, including sorbitol, propylene glycol, polyethylene glycol, glycerol or mixtures thereof, for example.

The formulations provided herein also may comprise about 0.001% to about 90%, or about 0.001% to about 50%, or about 0.001% to about 25%, or about 0.001% to about 10%, or about 0.001% to about 10% of one or more solvents or co-solvents to increase the solubility of any of the components of the present formulation. Solvents or co-solvents for use herein include, but are not limited to, hydroxylated solvents or other pharmaceutically- acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the formulations of the present invention may comprise one or more conventional diluents known in the art. The preferred diluent is purified water.

Tonicity agents may include, but are not limited to sodium chloride, potassium chloride, zinc chloride, calcium chloride or mixtures thereof. Other osmotic adjusting agents may also include, but are not limited to, mannitol, glycerol, and dextrose or mixtures thereof. In an alternative embodiment, the present formulation may comprise about 0.01% to about 8% w/w, or 1% to about 6% w/w, preferably about 5.0% w/w. The preferred tonicity agent is Dextrose, anhydrous.

In one alternative embodiment, the formulations of the present invention are stable. As used herein, the stability of formulations provided herein refers to the length of time at a given temperature that greater than 80%, 85%, 90% or 95% of the initial amount of drug substance, e.g., fluticasone, is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 25°. Also, in another alternative embodiment, using Arrhenius Kinetics, more than 80%, or more than 85%, or more than 90%, or more than 95% of the initial amount of drug substance (e.g., fluticasone) remains after storage of the formulations for more than 1, 2, 12, 18, 24 or 36 months between about 15° C. and about 30° C.

The formulations of the present invention may be manufactured in any conventional manner by thoroughly mixing the ingredients described herein at ambient or elevated temperatures in order to achieve solubility of ingredients where appropriate.

The preparation of a drug substance having the particle size distribution profile of the present invention may be obtained by any conventional means known in the art, or by minor modification of such means. For example, suspensions of drug particles can rapidly undergo particulate size reduction when subjected to "jet milling" (high pressure particle in liquid milling) techniques. Other known methods for reducing particle size into the micrometer range include mechanical milling, the application of ultrasonic energy and other techniques.

In one alternative embodiment, the present invention provides a method for the treatment of rhinitis comprising the step of administering to a subject in need thereof a therapeutically effective amount of the formulations disclosed herein. In one embodiment, the method of the present invention comprises administering to a subject in need thereof a therapeutically effective amount of drug substance, wherein the drug substance is fluticasone, the drug substance having a particle size distribution profile described herein. Preferably, the drug substance is fluticasone propionate. In certain embodiments, the subject is a mammal. In other embodiments, the subject is a human.

In one embodiment, the present invention provides a method for treating rhinitis comprising the step of administering to a subject in need thereof a therapeutically effective amount of the present formulation, wherein the formulation comprises an aqueous suspension comprising about 0.005% to about 5% by weight of fluticasone having a particle size distribution profile described herein. In certain embodiments, the formulation is sterile, contains a preservative and/or is stable.

In other embodiments, the present invention provides a method for treating rhinitis comprising the step of administering the formulations disclosed herein intranasally to a subject in need thereof. Preferably, the formulation is administered to a subject via nasal spray, preferably a metering, atomizing spray pump. Each actuation of the pump delivers a single dosage of the drug substance to the subject.

In another alternative embodiment, the present invention comprises a metering, atomizing spray pump unit comprising a microcrystalline suspension of fluticasone propionate. In another alternative embodiment, said suspension comprises microcrystalline cellulose, carboxymethyl cellulose sodium, dextrose, benzalkonium chloride, polysorbate 80, and about 0.25% v/w phenylethyl alcohol, has a pH between about 5 and 7. After initial priming (3-6 actuations), each actuation delivers from about 10 mcg to about 1,000 mcg, about 100 mcg to about 500 mcg, about 100 mcg to about 200 mcg, preferably about 50 mcg of fluticasone propionate through a nasal adapter. Each bottle containing the present formulations of nasal spray may provide about 20-600 metered sprays, preferably 100 to about 300 sprays, more preferably at least 100 metered sprays.

In an alternative embodiment, the administration of the present formulations may comprise 1, 2, 3, 4, 5, 6, 7 or 8 inhalations of the present formulation in each nostril one, two, three, four or five times a day. Each inhalation (spray) may comprise about 1 mcg to about 100 mcg, or about 1 mcg to about 100 mcg, preferably about 30 mcg to about 100 mcg, more preferably about 30 mcg to about 80 mcg, or about 50 mcg. The total dose per day of the drug substance may comprise about 10 mcg and about 1000 mcg, about 10 mcg to about 500 mcg, about 10 mcg to about 400 mcg, or about 10 mcg to about 300 mcg preferably about 100 mcg to about 200 mcg, or more preferably about 200 mcg.

In another alternative embodiment, the administration of the present formulations may comprise 1 and only 1 inhalation in each nostril a day. In one alternative embodiment, the starting dosage of the present formulations may comprise one and only 1 inhalation in each nostril once daily. In another alternative embodiment, such starting dosage is appropriate for adults. Each inhalation may comprise about 10 mcg to about 200 mcg, preferably about 100 mcg, more preferably about 50 mcg of fluticasone.

Administering 1 and only 1 inhalation in each nostril is more beneficial and advantageous over conventional regimens of the prior art, which require more inhalations in each nostril per day. For example, other known nasal spray products, e.g., fluticasone products, require 1 or 2 inhalations (42 to 84 mcg) in each nostril twice a day (total dose, 168-336 mcg/day). In contrast, formulations of the present invention may require 1 and only 1 inhalation in each nostril a day. By limiting the dosage, or amount of inhalations per day, individuals would likely comply with the regimen or regular dosage schedule to achieve adequate relief, thereby improving the patient's quality of life as compared with other traditional treatments. Also, administering fewer inhalations provide the individual more opportunity to take other medications during treatment, such as, for example, other oral or inhaled steroids, thus reducing likelihood of overdosing or cross reaction between medications. Further, providing fewer inhalations would reduce the likelihood of addiction to the drug substance in the nasal formulation. Moreover, administering fewer inhalations may reduce toxicity and the adverse events associated with 2 or more inhalations of a particular drug substance in each nostril per day. Also, individuals hypersensitive to 2 or more doses of a particular drug substance would benefit from receiving 1 and only 1 dose per day.

The present formulations can be packaged as kits or systems, which optionally contain other components, including instructions for use of the formulations. Articles of manufacture, containing packaging material and a formulation provided herein, which is useful for treatment, prevention or amelioration of one or more symptoms of a medical condition, disorder or disease (e.g. rhinitis) and a label indicating that the formulation is used for treatment, prevention or amelioration of one or more symptoms of diseases or disorders associated with undesired and/or uncontrolled rhinitis.

VI. EXAMPLE

The following example is included for illustrative purposes only and is not intended to limit the scope of the invention.

A blinded, randomized, placebo-controlled, multicenter study to assess the safety and efficacy of Dey Fluticasone Propionate Nasal Spray 50 mcg in adolescent and adult patients with seasonal allergic rhinitis was conducted. The primary objective of this study was to determine the safety and efficacy of Dey fluticasone propionate nasal spray 50 mcg (Dey-FP) compared with Placebo during 2 weeks of treatment in adult and adolescent patients with seasonal allergic rhinitis (SAR) due to mountain cedar pollen. The secondary objective was to establish the comparability of Dey-FP with FLONASE® Nasal Spray 50 mcg during 2 weeks of treatment in adults and adolescent patients with SAR due to mountain cedar pollen.

The study was a randomized, multicenter (7 sites), 3 treatment (Dey-FP, FLONASE®, and Placebo), 2 level (high and low dose) placebo-controlled repeated measures study conducted in the U.S. during the 2001/2002 mountain cedar pollen allergy season. The study duration was 3 weeks and consisted of 2 phases: a 1-week baseline screening period for diary data followed by a 2-week randomized patient- and rater-blind treatment phase. Patients were seen on an outpatient basis on Day-7, Day 1, Day 7, and Day 14. The initial baseline screening period for diary data began 1 week (Day-7±2 days) prior to randomization to treatment. Patients who met the eligibility criteria (inclusion/exclusion criteria and completion of baseline study procedures [within 30 days of Day-7]) were assigned a patient number, given standard oral antihistamine as a rescue medication, and a Patient Total Nasal Symptom Score (TNSS) Diary. Patients recorded daily TNSS (sum of the signs and symptoms for runny nose, nasal congestion, sneezing, and itchy nose) in their diaries rating each on a scale of 0 to 3 with 0 being no symptoms present and 3 being severe symptoms present. The amount of oral antihistamine taken was recorded as well.

One week later, at the conclusion of the baseline screening period, the patients returned to the study site and were re-evaluated for eligibility. Patients who did not complete the diaries or no longer met the entry criteria were discontinued. Patients who met all entry criteria were then randomized to 1 of 6 treatment groups: Dey-FP High Dose, Dey-FP Low Dose, FLONASE High Dose, FLONASE Low Dose, or Placebo High Dose or Placebo Low Dose. The patient- and rater-blind treatment phase (Day 1 through 14) consisted of once daily self-administered treatment (1-2 sprays into each nostril per administration). On Days 7 and 14 (or at early termination), patients returned to the study sites and were evaluated. Efficacy assessments included reflective and instantaneous TNSS daily diary information, patient and physician global evaluations, and use of rescue medication. Safety evaluations were the incidence of adverse events, clinical laboratory tests, physical examinations findings, vital signs measurements, and ECG results (see Study Flow Chart). Pollen counts, outside air temperature, rainfall, and humidity were also monitored and recorded by each study site.

- A history of moderate-to-severe SAR due to mountain cedar pollen for at least 2 years individuals 12 years of age and older;
- Confirmed IgE-mediated hypersensitivity to mountain cedar pollen within last 12 months (a positive result is required);
- Minimum TNSS of 8 out of a maximum of 12 (either AM or PM 12-hour assessment) on at least 3 days during the baseline period, one of which must have been within 3 days of Day 1;
- If receiving immunotherapy, a stable maintenance regimen for 30 days prior to study enrollment;
- General good health and free of disease or concomitant treatment that could interfere with interpretation of study results;
- Written informed consent/pediatric assent; and
- Willingness to comply with study procedures.

Patients who met all criteria were then randomized to 1 of 6 treatment groups: (1) Dey-FP 50 mcg Low Dose (100 mcg)—1 spray in each nostril daily; (2) Dey-FP 50 mcg High Dose (100 mcg)—1 spray in each nostril twice daily; (3) FLONASE® Nasal Spray Low Dose (100 mcg)—1 spray in each nostril daily; (4) FLONASE® Nasal Spray High Dose (200 mcg)—1 spray in each nostril daily twice daily; (5) placebo—1 spray in each nostril once daily; and, (6) placebo—1 spray in each nostril twice daily.

The primary endpoint for this study was the change from baseline in a patient's combined (AM and PM) 12-hour reflective TNSS over a 2-week treatment period. The primary endpoint analysis was the comparison of Dey-FP Low Dose versus Placebo High and Low Dose overall (Days 2-14) and at Days 7 and 14. TNSS consisted of the sum of the combined AM plus PM 12-hour assessment scores for runny nose, nasal congestion, sneezing, and itchy nose recorded twice daily on the Patient's TNSS Diary card. Baseline was defined as the average of the run-in period of the combined (AM plus PM) 12-hour reflective TNSS from the 7 calendar days ±2 days preceding Day 1.

Secondary endpoints for this study included:

The change from baseline in a patient's combined (AM plus PM) 12-hour reflective TNSS overall (Days 2-14);

The change from baseline in a patient's combined (AM plus PM) 12-hour reflective TNSS at Days 7 and 14;

The change from baseline in a patient's AM 12-hour reflective TNSS;

The change from baseline in a patient's PM 12-hour reflective TNSS;

The percent change from baseline in a patient's combined (AM plus PM) 12-hour reflective TNSS;

The percent change from baseline in a patient's AM 12-hour reflective TNSS;

The percent change from baseline in a patient's PM 12-hour reflective TNSS;

The change from baseline to 1-week and 2-week post-baseline in area under the curve (AUC) of patient's combined (AM plus PM) 12-hour reflective TNSS;

The change from baseline to 1-week and 2-week post-baseline in area under the curve (AUC) of patient's AM 12-hour reflective TNSS;

The change from baseline to 1-week and 2-week post-baseline in area under the curve (AUC) of patient's PM 12-hour reflective TNSS;

The change from baseline in patient's combined (AM plus PM) instantaneous TNSS;

The change from baseline in patient's AM instantaneous TNSS;

The change from baseline in patient's PM instantaneous TNSS;

Patient global evaluation of change in SAR signs and symptoms;

Physician global evaluation of change in SAR signs and symptoms; and

Use of rescue medication.

Secondary Efficacy Endpoints were Compared Across all Treatment Groups.

Both reflective and instantaneous change from baseline in 12-hour (AM plus PM, combined and individual) TNSS for primary and secondary variables were compared across treatment groups using a mixed effect analysis of variance (ANOVA) model with Treatment, day (Days 2-14) and the interaction of Treatment-by-Day as fixed effects and patients as random effect. Area under the curve (AUC) of the 12-hour (AM plus PM, combined and individual) reflective TNSS was calculated for the baseline period and Week 1 and Week 2 postbaseline using a trapezoidal method. The change from baseline in AUC was compared across the groups using a similar ANOVA model as described for the primary efficacy variable. Patient and physician global evaluations of change from baseline in SAR symptoms were compared between the groups using a one-way ANOVA model. Frequency of rescue medication use, as well as the percentage of patients needing rescue medication, was compared across the groups using the Pearson Chi-square test. The average number of tablets of rescue medication was compared using an ANOVA model. All statistical analyses were performed for both Intent-to-Treat (ITT) and Per Protocol (PP) Populations. TNSS missing observations in the ITT Population were imputed using the last observation carried forward (LOCF) method. All inferential statistics were conducted against a two-sided alternative hypothesis at 0.05 level of significance.

In all, 774 patients were enrolled and randomized to 1 of 6 treatment groups at 7 study centers located in the US during the 2001/2002 mountain cedar pollen allergy season, including 1 patient who enrolled at 2 separate sites (Patient 02-044 and 05-056 were the same patient). The data from Patient 02-044 were excluded from all analysis populations except the randomized patient population because the patient had received study drug. The data from Patient 05-056 were included in the analysis populations because enrollment at Site 5 preceded enrollment at the second site, Site 2. The Intent-to-Treat (ITT) Population, therefore, was composed of 773 patients (774 randomized patients minus Patient 02-044). The distribution was as follows: 129 patients in the Dey-FP High Dose group, 129 in the Dey-FP Low Dose group, 127 in the FLONASE High Dose group, 129 in the FLONASE Low Dose group, 131 in the Placebo High Dose group, and 128 patients in the Placebo Low Dose group. In total, 752 (97.3%) patients of the original 774 completed the study and 22 (2.8%) discontinued prematurely, 8 of these were due to Aes. Patients were predominantly White (>90%) and female (>59%). The mean age range was from 37.55 to 42.01 years (min-max range=12.1 to 78.9 years) across treatment groups. Patients had a mean skin antigen challenge score of between 7.5 to 8.5 mm. Over half of all patients (>58%) had no previous history of fluticasone usage.

All active treatment groups (Dey-FP and FLONASE) demonstrated reductions in TNSS over the 2-week treatment period. Regardless of which efficacy endpoint was examined (i.e., 12-hour reflective TNSS, instantaneous TNSS, change in AUC), the Treatment effect was highly significant as was the day (duration of treatment) effect (p=0.0000) indicating improvement in TNSS. Both Dey-FP and FLONASE Low Dose groups were statistically superior to Placebos for both primary and secondary efficacy endpoint analyses, as were Dey-FP High Dose and FLONASE High Dose treatment groups. Treatment-by-Day interaction (overall Days 2-14) and Treatment-by-Week interaction (Week 1 and Week 2) effects were not statistically significant indicating that the treatment groups behaved similarly for the duration of the study, except for the magnitude of improvement in TNSS. There was no statistically significant differences between Dey-FP and FLONASE High and Low Dose groups for any efficacy endpoint analysis (relief of signs and symptoms of SAR). Moreover, all active treatment groups were consistently statistically superior to both High and Low Dose Placebo groups. Results of analyses for the Per Protocol Population paralleled those of the ITT Population for all efficacy variables.

Figure 2:
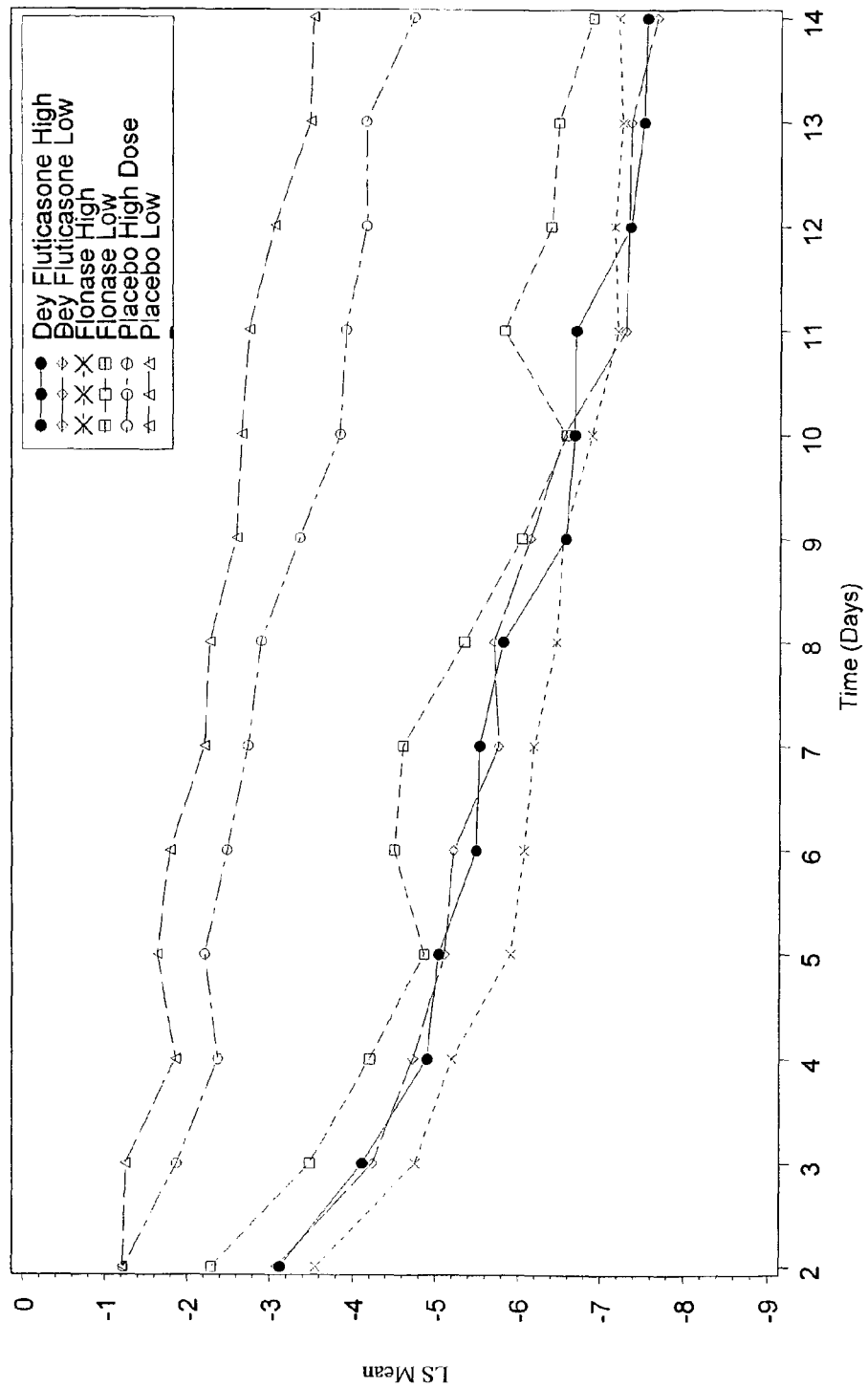
FIG. 2 shows the change from baseline in AM and PM reflective TNSS over time in the PP population over a 14 day study period.
Figure 4:
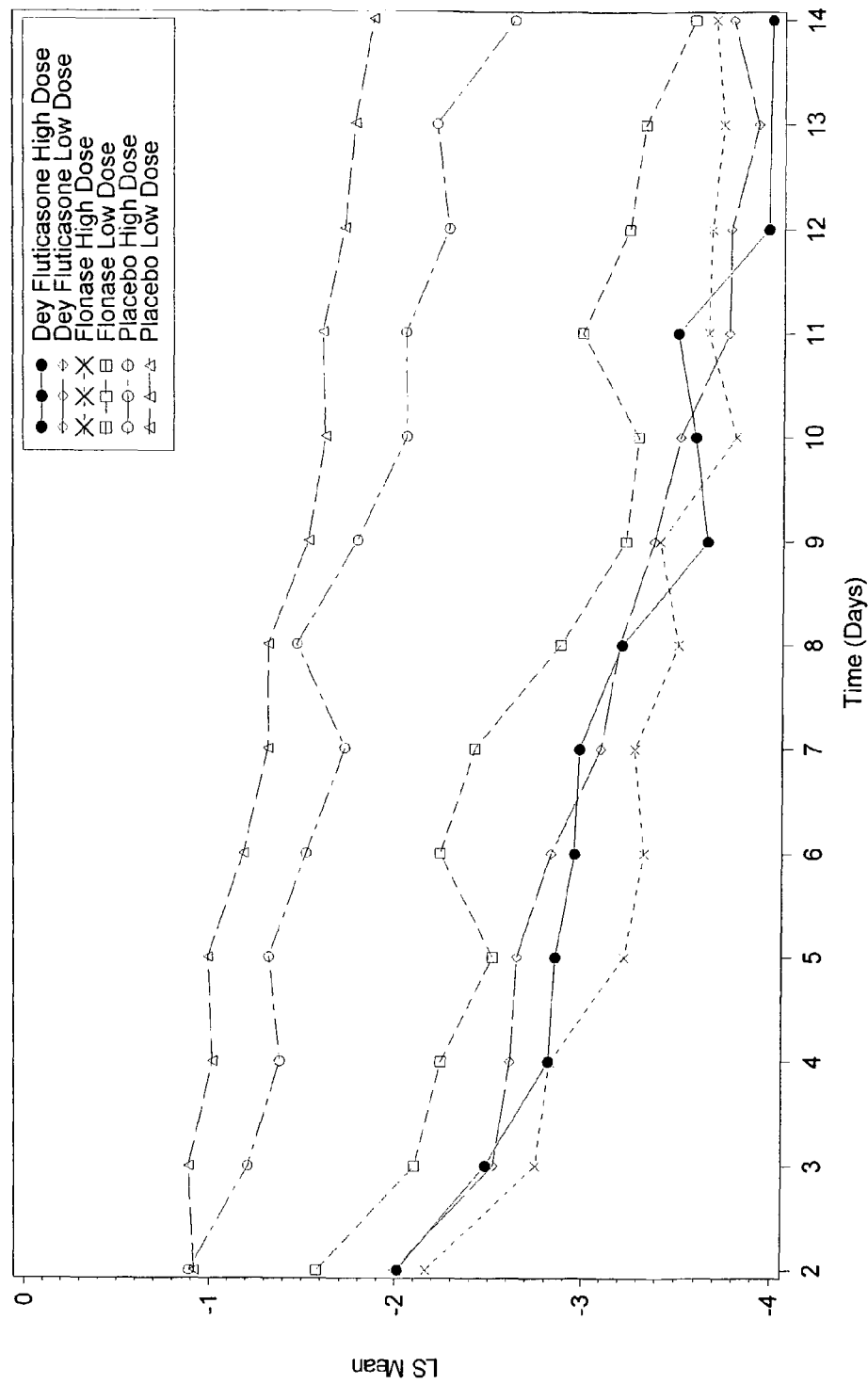
FIG. 4 shows the change from baseline in PM reflective TNSS over time in the PP population over a 14 day study period.

In FIGS. 1-4, the efficacy of the nasal formulations is expressed as the change from baseline (pretreatment) in a composite score of nasal symptoms (e.g. runny nose, sneezing, nasal itching and congestion) referred to as total nasal symptom scores (TNSS). The change from baseline in TNSS scores is expressed in absolute units (rather tan percent change from baseline). Using an analysis of variance model (ANOVA), the least square mean (LS Mean) for the baseline (positive value) and change from baseline (negative value if symptoms improve) are obtained. The higher the negative value seen in the LS Mean, the greater was the change (improvement) in TNSS.

Table 1 shows a particle size distribution of the fluticasone particles in Dey-FP, wherein the particle size is in microns. Table 2 also shows the particle size distribution of fluticasone particles of another batch of Dey-FP, wherein the particle size is in microns. Table 3 shows the formulation of Dey-FP.

TABLE 1

Dey-FP 50 mcg
Particle Size Data—Batch 1

|           | Run 1 | Run 2 | Run 3 | Avg  |
|-----------|-------|-------|-------|------|
| D (v, 0.10) | 0.38  | 0.38  | 0.41  | 0.39 |
| D (v, 0.25) | 0.75  | 0.75  | 0.78  | 0.76 |
| D (v, 0.50) | 1.50  | 1.51  | 1.56  | 1.52 |
| D (v, 0.75) | 2.93  | 2.94  | 3.05  | 2.97 |
| D (v, 0.90) | 5.22  | 5.21  | 5.42  | 5.28 |

TABLE 2

Dey-FP 50 mcg
Particle Size Data—Batch 2

|           | Run 1 | Run 2 | Run 3 | Avg  |
|-----------|-------|-------|-------|------|
| D (v, 0.10) | 0.38  | 0.42  | 0.37  | 0.39 |
| D (v, 0.25) | 0.76  | 0.79  | 0.72  | 0.76 |
| D (v, 0.50) | 1.53  | 1.57  | 1.40  | 1.50 |
| D (v, 0.75) | 3.00  | 3.08  | 2.64  | 2.91 |
| D (v, 0.90) | 5.34  | 5.50  | 4.53  | 5.12 |

TABLE 3

Formulation of Fluticasone Propionate Nasal Spray

| INGREDIENT | FUNCTION | DRUG PRODUCT CONCENTRATION | PER SPRAY | PER BOTTLE |
|---|---|---|---|---|
| Fluticasone Propionate USP | Active Ingredient | 0.050% w/w | 0.050 mg | 8.00 mg |
| Benzalkonium Choloride Solution 50% NF | Preservative | 0.020% w/w | 0.0388 mg | 6.21 mg |
| Microcrystalline Cellulose/Carboxymethy-cellose Sodium NF | Suspension Agent | 1.50% w/w | 1.50 mg | 240.0 mg |
| Polysorbate 80 NF | Wetting Agent | 0.005% w/w | 0.005 mg | 0.80 mg |
| Phenylethyl Alcohol USP | Preservative | 0.25% v/w | 0.255 mg | 40.80 mg |
| Dextrose, Anhydrous USP | To adjust osmolality | 5.00% w/w | 5.00 mg | 800.0 mg |
| Hydrochloric Acid 1N | To adjust pH | As required | As required | As required |
| Purified Water USP | Diluent | n/a | 93.15 mg | 14.90 g |

The Figures and attachments herein are presented for illustrative purposes only. They are not intended to limit the scope of the invention. Further, it should be understood that various changes and modifications to the presently preferred embodiment described herein will be apparent to those skilled in the art. Such changes and modifications can be made without departing from the spirit and scope of the present invention and without diminishing its attendant advantages. It is therefore intended that such changes and modifications be covered by the appended claims. Also, the invention may suitably comprise, consist of or consist essentially of the elements or steps described herein. Further, the invention described herein suitably may comprise or be practiced in the absence of any element or step which is not specifically disclosed herein. Further, one or more step described herein may be performed simultaneously with another step.

What is claimed is:

1. A nasal pharmaceutical formulation comprising an aqueous suspension of a therapeutically effective amount of fluticasone propionate, wherein the aqueous suspension comprises 0.04% to 0.06% by weight of suspended solid fluticasone propionate particles having the following particle size distribution profile:
   about 10% of the solid fluticasone particles have a particle size of less than 0.4 microns;
   about 25% of the solid fluticasone particles have a particle size of less than 0.75 microns;
   about 50% of the solid fluticasone particles have a particle size of less than 1.5 microns;
   about 75% of the solid fluticasone particles have a particle size of less than 3.0 microns; and
   about 90% of the solid fluticasone particles have a particle size of less than 5.3 microns;
   wherein the fluticasone is suitable for administration to an individual intranasally,
   wherein the formulation further comprises a complexing agent selected from the group consisting of ethylenediaminetetraacetic acid (EDTA), citric acid, nitrilotriacetic acid, and salts thereof,
   and wherein greater than 95% of the fluticasone originally present in the formulation remains in the formulation after storage for 12 months at a temperature between 15 to 30° C.; and
   wherein the formulation further comprises the following compounds:
      (a) microcrystalline cellulose;
      (b) carboxymethyl cellulose sodium;
      (c) dextrose;
      (d) benzalkonium chloride;
      (e) polysorbate 80; and
      (f) phenylethyl alcohol;
   wherein the formulation further comprises zinc chloride; and
   wherein the formulation is sterile.

2. The formulation of claim 1, wherein the formulation comprises 0.05% by weight of the suspended solid fluticasone propionate particles.

3. The formulation of claim 1, wherein the formulation is in a metered-dose spray pump bottle.

4. The formulation of claim 1, wherein the nasal pharmaceutical formulation comprises about 0.04% to about 0.045% by weight of the suspended solid fluticasone propionate particles.

5. A system for the treatment of one or more symptoms of rhinitis, said system comprising:
   (a) a pre-packaged formulation, said formulation comprising an aqueous suspension comprising about 0.04% to 0.06% by weight of suspended solid fluticasone propionate particles, wherein the suspended solid fluticasone propionate particles have the following particle size distribution profile:
(i) about 10% of the solid fluticasone particles have a particle size of less than 0.4 microns;
(ii) about 25% of the solid fluticasone particles have a particle size of less than 0.75 microns;
(iii) about 50% of the solid fluticasone particles have a particle size of less than 1.5 microns;
(iv) about 75% of the solid fluticasone particles have a particle size of less than 3.0 microns; and
(v) about 90% of the solid fluticasone particles have a particle size of less than 5.3 microns;
wherein the fluticasone is suitable for administration to an individual intranasally,
wherein the formulation further comprises a complexing agent selected from the group consisting of ethylenediaminetetraacetic acid (EDTA), citric acid, nitrilotriacetic acid, and salts thereof,
wherein greater than 95% of the fluticasone originally present in the formulation still remains in the formulation after storage for 12 months at a temperature between 15 to 30° C.;
wherein the formulation further comprises the following compounds:
(a) microcrystalline cellulose;
(b) carboxymethyl cellulose sodium;
(c) dextrose;
(d) benzalkonium chloride;
(e) polysorbate 80; and
(f) phenylethyl alcohol;
wherein the formulation further comprises zinc chloride; and
wherein the formulation is sterile.

6. The system of claim 5, wherein the formulation is in a metered-dose spray pump bottle.

7. The system of claim 6, wherein each spray of the metered-dose spray pump delivers at least about 1 mcg of the fluticasone propionate.

8. The system of claim 6, wherein each spray of the metered-dose spray pump delivers about 1 mcg to about 100 mcg of the fluticasone propionate.

9. An aqueous nasal spray formulation comprising an aqueous suspension of 0.04% to 0.06% by weight of suspended solid fluticasone propionate particles, wherein the aqueous suspension has the following suspended solid particle size distribution profile:
about 10% of the solid fluticasone particles have a particle size of less than 0.4 microns;
about 25% of the solid fluticasone particles have a particle size of less than 0.75 microns;
about 50% of the solid fluticasone particles have a particle size of less than 1.5 microns;
about 75% of the solid fluticasone particles have a particle size of less than 3.0 microns; and
about 90% of the solid fluticasone particles have a particle size of less than 5.3 microns;
wherein the fluticasone is suitable for administration to an individual intranasally,
wherein the formulation further comprises a complexing agent selected from the group consisting of ethylenediaminetetraacetic acid (EDTA), citric acid, nitrilotriacetic acid, and salts thereof,
wherein greater than 95% of the fluticasone originally present in the formulation still remains in the formulation after storage for 12 months at a temperature between 15 to 30° C.;
wherein the formulation further comprises the following compounds:
(a) microcrystalline cellulose;
(b) carboxymethyl cellulose sodium;
(c) dextrose;
(d) benzalkonium chloride;
(e) polysorbate 80; and
(f) phenylethyl alcohol;
wherein the formulation further comprises zinc chloride; and
wherein the nasal spray formulation is sterile.

10. The formulation of claim 9, wherein the formulation comprises 0.05% by weight of the suspended solid fluticasone propionate particles.

11. The formulation of claim 9, wherein the formulation is in a metered-dose spray pump bottle.

12. The formulation of claim 9, wherein the nasal spray formulation comprises about 0.04% to about 0.045% by weight of the fluticasone propionate.

13. An aqueous nasal spray formulation comprising:
an aqueous suspension of suspended solid fluticasone propionate particles; wherein the formulation comprises 0.04% to 0.06% by weight of fluticasone propionate particles having the following solid particle size distribution profile:
D10 is 0.39 microns;
D25 is 0.76 microns;
D50 is 1.52 microns;
D75 is 2.97 microns; and
D90 is 5.28 microns,
wherein the formulation further comprises a complexing agent selected from the group consisting of ethylenediaminetetraacetic acid (EDTA), citric acid, nitrilotriacetic acid, and salts thereof,
wherein greater than 95% of the fluticasone originally present in the formulation still remains in the after storage for 12 months at a temperature between 15 to 30° C.;
wherein the nasal spray formulation further comprises the following compounds:
(a) microcrystalline cellulose;
(b) carboxymethyl cellulose sodium;
(c) dextrose;
(d) benzalkonium chloride;
(e) polysorbate 80; and
(f) phenylethyl alcohol;
wherein the formulation further comprises zinc chloride; and
wherein the nasal spray formulation is sterile.

14. The aqueous nasal spray formulation of claim 13, wherein the nasal spray formulation is placed in a metered-dose, manual pump spray unit.

15. The formulation of claim 13, wherein the formulation is in a metered-dose spray pump bottle.

16. The formulation of claim 13, wherein the nasal spray formulation comprises about 0.04% to about 0.045% by weight of the fluticasone propionate.

17. The formulation of claim 1, wherein the complexing agent is sodium edetate.

* * * * *